US008084416B2

(12) United States Patent
Sampson et al.

(10) Patent No.: US 8,084,416 B2

(45) Date of Patent: Dec. 27, 2011

(54) AXMI-150 DELTA-ENDOTOXIN GENE AND METHODS FOR ITS USE

(75) Inventors: Kimberly S. Sampson, Durham, NC (US); Daniel J. Tomso, Bahama, NC (US); Volker Heinrichs, Raleigh, NC (US)

(73) Assignee: Athenix Corp., Morrisville, NC (US)

( * ) Notice: Subject to any disclaimer, the term of this patent is extended or adjusted under 35 U.S.C. 154(b) by 0 days.

(21) Appl. No.: 12/646,004

(22) Filed: Dec. 23, 2009

(65) Prior Publication Data

US 2010/0160231 A1 Jun. 24, 2010

Related U.S. Application Data

(60) Provisional application No. 61/140,427, filed on Dec. 23, 2008.

(51) Int. Cl.
*C07K 14/00* (2006.01)
*A01N 33/00* (2006.01)
*A01P 15/00* (2006.01)

(52) U.S. Cl. ................................ 514/2; 514/12; 530/350

(58) Field of Classification Search ................ 514/2, 12; 530/300, 324, 350; 424/9.1
See application file for complete search history.

(56) References Cited

U.S. PATENT DOCUMENTS

| | | | | |
|---|---|---|---|---|
| 5,380,831 | A | 1/1995 | Adang et al. | |
| 5,866,784 | A | 2/1999 | Van Mellaert et al. | |
| 5,908,970 | A | 6/1999 | Van Mellaert et al. | |
| 6,172,281 | B1 | 1/2001 | Van Mellaert et al. | |
| 6,177,615 | B1 | 1/2001 | Baum | |
| 6,833,449 | B1 | 12/2004 | Barton et al. | |
| 7,355,099 | B2 | 4/2008 | Carozzi et al. | |
| 2001/0003849 | A1 | 6/2001 | Barton et al. | |
| 2004/0197916 | A1 | 10/2004 | Carozzi et al. | |
| 2008/0040827 | A1 | 2/2008 | Donovan et al. | |
| 2008/0172764 | A1 | 7/2008 | Carozzi et al. | |
| 2008/0176801 | A1 | 7/2008 | Carozzi et al. | |
| 2009/0099081 | A1 | 4/2009 | Carozzi et al. | |
| 2010/0077507 | A1* | 3/2010 | Abad et al. .................... | 800/279 |

FOREIGN PATENT DOCUMENTS

| | | |
|---|---|---|
| WO | 2004/074462 | 9/2004 |
| WO | WO 2004/074462 A2 | 9/2004 |
| WO | 2005/107383 | 11/2005 |
| WO | WO 2005/107383 A2 | 11/2005 |

OTHER PUBLICATIONS

Angsuthanasombat, C., et al., "Directed Mutagenesis of the *Bacillus thuringiensis* Cry11A Toxin Reveals a Crucial Role in Larvicidal Activity of Arginine-136 in Helix 4," *J. Biochem. Mol. Biol.*, Sep. 2001, pp. 402-407, vol. 34, No. 5.

Aronson, A.I., and Shai, Y., "Why *Bacillus thuringiensis* Insecticidal Toxins are so Effective: Unique Features of Their Mode of Action," *FEMS Microbiology Letters*, 2001, pp. 1-8.

De Maagd, R.A., et al., "Identification of *Bacillus thuringiensis* Delta-Endotoxin Cry1C Domain III Amino Acid Residues Involved in Insect Specificity," *Appl. Environ. Microbiol.*, Oct. 1999, pp. 4369-4374, vol. 65, No. 10.

De Maagd, R.A., et al., "How *Bacillus thuringiensis* has Evolved Specific Toxins to Colonize the Insect World," Trends Genet., Apr. 2001, pp. 193-199, vol. 17, No. 4.

Guo, H.H., et al., "Protein Tolerance to Random Amino Acid Change," *PNAS*, Jun. 22, 2004, pp. 9205-9210, vol. 101, No. 25.

Hill, M.A. and Preiss, J., "Functional Analysis of Conserved Histidines in ADP-Glucose Pyrophosphorylase from *Escherichia coli," Biochem. Biophys. Res. Comm.*, Mar. 1998, pp. 573-577, vol. 244.

Honée, G., et al., "Nucleotide Sequence of Crystal Protein Gene Isolated from *B. thuringiensis* subspecies *entomocidus* 60.5 Coding for a Toxin Highly Active Against *Spodoptera* Species," *Nucleic Acids Research*, May 13, 1988, p. 6240, vol. 16, No. 13.

Jenkins, J.L., et al., "Binding of *Bacillus thuringiensis* CrylAc Toxin to *Manduca sexta* Aminopeptidase-N Receptor is Not Directly Related to Toxicity," *FEBS Letters*, 1999, pp. 373-376, vol. 462.

Kalman, et al., "Cloning of a Novel *cryIC*-type Gene from a Strain of *Bacillus thuringiensis* subsp. *galleriae," Applied and Environmental Microbiology*, 1993, pp. 1131-1137, vol. 59, No. 4.

Lazar, E., et al., "Transforming Growth Factor α: Mutation of Aspartic Acid 47 and Leucine 48 Results in Different Biological Activities," *Mol. Cell. Biol.*, Mar. 1988, pp. 1247-1252, vol. 8, No. 3.

Lee, M.K., et al., "Mutations at the Argine Residues in α8 Loop of *Bacillus thuringiensis* δ-endotoxin CrylAc Affect Toxicity and Binding to *Manduca sexta* and *Lymantria dispar* Aminopepidase N," *FEBS Letters*, 2001, pp. 108-112, vol. 497.

Masson, L., et al., "Mutagenic Analysis of a Conserved Region of Domain III in the CrylAc Toxin of *Bacillus thuringiensis," Appl. Environ. Microbiol.*, Jan. 2002, pp. 194-200, vol. 68, No. 1.

Rajamohan, F., et al., "Mutations at Domain II, Loop 3, of *Bacillus thuringiensis* CrylAa and CrylAb δ-Endotoxins Suggest Loop 3 is Involved in Initial Binding to Lepidopteran Midguts," *J. Biol. Chem.*, Oct. 11, 1996, pp. 25220-25226, vol. 271, No. 41.

Sanchis, V., et al., "Nucleotide Sequence and Analysis of the N-terminal Coding Region of the Spodoptera-active δ-endotoxin Gene of *Bacillus thuringiensis aizawai* 7.29," *Mol. Microbiol.*, 1989, pp. 229-238, vol. 3, No. 2.

Schwartz, J.L., et al., "Single-Site Mutations in the Conserved Alternating-Arginine Region Affect Ionic Channels Formed by CrylAa, a *Bacillus thuringiensis* Toxin," *Appl. Environ. Microbiol.*, Oct. 1997, pp. 3978-3984, vol. 63, No. 10.

Tounsi, S., et al., "Cloning and Study of the Expression of a Novel cryl*la*-type Gene from *Bacillus thuringiensis subsp. Kurstaki," J. Appl. Microbiol.* 2003, pp. 23-28, vol. 95.

(Continued)

*Primary Examiner* — Chih-Min Kam
(74) *Attorney, Agent, or Firm* — Destiny M. Davenport

(57) ABSTRACT

Compositions and methods for conferring pesticidal activity to bacteria, plants, plant cells, tissues and seeds are provided. Compositions including a coding sequence for pesticidal polypeptides are provided. The coding sequences can be used in DNA constructs or expression cassettes for transformation and expression in plants and bacteria. Compositions also include transformed bacteria, plants, plant cells, tissues, and seeds. In particular, isolated pesticidal nucleic acid molecules are provided. Additionally, amino acid sequences corresponding to the polynucleotides are encompassed. In particular, the present invention provides for isolated nucleic acid molecules having nucleotide sequences encoding the amino acid sequence shown in SEQ ID NO:2, the nucleotide sequence set forth in SEQ ID NO:1, 3, 4, 5, 6, 7, 8, 9, 10, 11, or 12, as well as variants and fragments thereof.

9 Claims, No Drawings

OTHER PUBLICATIONS

NCBI Database Report for Accession No. AAA22343, 1991.

NCBI Database Report for Accession No. AAF37224, Direct Submission on Dec. 14, 1999.

NCBI Database Report for Accession No. AAM00264, Direct Submission on Mar. 16, 2001.

NCBI Database Report for Accession No. AAN16462, Direct Submission on Aug. 22, 2002.

NCBI Database Report for Accession No. CAA65457, Direct Submission on Mar. 18, 1996.

Database UniProt Jun. 16, 2009, "SubNarne: Full=Pesticidal crystal protein cry1Bc;" XP002573546 retrieved from EBI accession No. UNIPROT: C3IAA7.

Invitation to Pay Additional Fees and Partial Search Report of PCT/US2009/069381 dated Apr. 1, 2010, (4 pages).

* cited by examiner

SEQUENCE LISTING

```
<160> NUMBER OF SEQ ID NOS: 14

<210> SEQ ID NO 1
<211> LENGTH: 2028
<212> TYPE: DNA
<213> ORGANISM: Bacillus thuringiensis
<220> FEATURE:
<221> NAME/KEY: CDS
<222> LOCATION: (1)...(2028)

<400> SEQUENCE: 1

ttg gag gaa aga agt atg aac tca aat gaa cat gat tat ttg aaa gtt       48
Met Glu Glu Arg Ser Met Asn Ser Asn Glu His Asp Tyr Leu Lys Val
 1               5                   10                  15

tgt gat gat tta agt gaa act aat atg gag agg ttt gac aaa aat gat       96
Cys Asp Asp Leu Ser Glu Thr Asn Met Glu Arg Phe Asp Lys Asn Asp
             20                  25                  30

gca ctg gag att ggt atg tct att gta tct gaa ctt ctt ggc atg att      144
Ala Leu Glu Ile Gly Met Ser Ile Val Ser Glu Leu Leu Gly Met Ile
         35                  40                  45

cca ggc gga gca gcc tta caa ttt gtg ttt aat caa ttg tgg tcg cgt      192
Pro Gly Gly Ala Ala Leu Gln Phe Val Phe Asn Gln Leu Trp Ser Arg
     50                  55                  60

tta ggt gat tct gga tgg agt gca ttc atg gaa cat gtt gaa gaa tta      240
Leu Gly Asp Ser Gly Trp Ser Ala Phe Met Glu His Val Glu Glu Leu
 65                  70                  75                  80

att gat act aaa ata gaa ggg tat gca aaa aat aaa gcc tta tct gag      288
Ile Asp Thr Lys Ile Glu Gly Tyr Ala Lys Asn Lys Ala Leu Ser Glu
                 85                  90                  95

tta gca ggt atg cac aga aat ctt gaa aca tat ata aaa ttg ctt aat      336
Leu Ala Gly Met His Arg Asn Leu Glu Thr Tyr Ile Lys Leu Leu Asn
            100                 105                 110

gaa tgg gaa aat aat act gga agt tca aaa gca caa ggt aga gta gct      384
Glu Trp Glu Asn Asn Thr Gly Ser Ser Lys Ala Gln Gly Arg Val Ala
        115                 120                 125

aat tat ttt gaa agt ctt gag cag gcg gtt gaa aga ggt atg cct caa      432
Asn Tyr Phe Glu Ser Leu Glu Gln Ala Val Glu Arg Gly Met Pro Gln
    130                 135                 140

ttc gca gtt ggt aat ttc gaa ata ccc ctt tta act gtt tat gta caa      480
Phe Ala Val Gly Asn Phe Glu Ile Pro Leu Leu Thr Val Tyr Val Gln
145                 150                 155                 160

gct gct aac ctt cat tta ttg tta tta aga gat gtt tca gtt tat gga      528
Ala Ala Asn Leu His Leu Leu Leu Leu Arg Asp Val Ser Val Tyr Gly
                165                 170                 175

aaa cgc tgg gga tgg tca gat cag aaa att aag att tat tat gag aaa      576
Lys Arg Trp Gly Trp Ser Asp Gln Lys Ile Lys Ile Tyr Tyr Glu Lys
```

-continued

```
            180                 185                 190

caa gtt aag tat act cat gaa tac acc aat cat tgt tcg act tgg tat      624
Gln Val Lys Tyr Thr His Glu Tyr Thr Asn His Cys Ser Thr Trp Tyr
        195                 200                 205

aat aga gga cta gat aaa ttg aaa aat aag ggt tct tct tac caa gat      672
Asn Arg Gly Leu Asp Lys Leu Lys Asn Lys Gly Ser Ser Tyr Gln Asp
    210                 215                 220

tgg tac aac tat aat cgt ttc cgt aga gaa att act ctt act gtt cta      720
Trp Tyr Asn Tyr Asn Arg Phe Arg Arg Glu Ile Thr Leu Thr Val Leu
225                 230                 235                 240

gat atc gtc gct gta ttc cca cac tat gat gtg aaa gct tat cca att      768
Asp Ile Val Ala Val Phe Pro His Tyr Asp Val Lys Ala Tyr Pro Ile
                245                 250                 255

caa aca gtt ggc caa tta aca agg gaa gtt tat aca gac cct tta att      816
Gln Thr Val Gly Gln Leu Thr Arg Glu Val Tyr Thr Asp Pro Leu Ile
            260                 265                 270

aat ttt aat ccg caa cta gat tct gta tct caa tta cct act ttt agt      864
Asn Phe Asn Pro Gln Leu Asp Ser Val Ser Gln Leu Pro Thr Phe Ser
        275                 280                 285

gat atg gaa aat gca aca att aga acc cca cat ctg atg gag ttt tta      912
Asp Met Glu Asn Ala Thr Ile Arg Thr Pro His Leu Met Glu Phe Leu
    290                 295                 300

aga atg cta aca atc tat aca gat tgg tat agt gtg gga aga aac tat      960
Arg Met Leu Thr Ile Tyr Thr Asp Trp Tyr Ser Val Gly Arg Asn Tyr
305                 310                 315                 320

tat tgg gga gga cat cga gtg act tct tac cgt gta gga gga gaa aat     1008
Tyr Trp Gly Gly His Arg Val Thr Ser Tyr Arg Val Gly Gly Glu Asn
                325                 330                 335

ata acc tcc cct tta tat gga agt gag gca aat caa gag ctg cct aga     1056
Ile Thr Ser Pro Leu Tyr Gly Ser Glu Ala Asn Gln Glu Leu Pro Arg
            340                 345                 350

caa ctg tat ttt tat ggg ccg gtt ttt aga aca tta tca aat cct act     1104
Gln Leu Tyr Phe Tyr Gly Pro Val Phe Arg Thr Leu Ser Asn Pro Thr
        355                 360                 365

tta aga tac tta cag caa cct gcg cca gct ccg ccg ttt gct tta cgt     1152
Leu Arg Tyr Leu Gln Gln Pro Ala Pro Ala Pro Pro Phe Ala Leu Arg
    370                 375                 380

cgc tta gaa gga gta gaa ttt cac acc act aca ggt act gat atg tat     1200
Arg Leu Glu Gly Val Glu Phe His Thr Thr Thr Gly Thr Asp Met Tyr
385                 390                 395                 400

cgt gaa aga gga tcg gta gat tct ttt aat gag cta ccg cct ttt aat     1248
Arg Glu Arg Gly Ser Val Asp Ser Phe Asn Glu Leu Pro Pro Phe Asn
                405                 410                 415

cca gtt gga cta cct cgt aat gca tat agt cac cgt tta tgt cat gca     1296
Pro Val Gly Leu Pro Arg Asn Ala Tyr Ser His Arg Leu Cys His Ala
            420                 425                 430

acg ttt gtc cgt aaa tct ggg acc cct tat cta ata acc ggt act gtc     1344
Thr Phe Val Arg Lys Ser Gly Thr Pro Tyr Leu Ile Thr Gly Thr Val
        435                 440                 445

ttt tct tgg aca cat cgt agt gct gaa gaa acc aat aca att gat tca     1392
Phe Ser Trp Thr His Arg Ser Ala Glu Glu Thr Asn Thr Ile Asp Ser
    450                 455                 460

aat aga atc acg caa att cca ttg gtg aaa gca tat caa att agc tcg     1440
Asn Arg Ile Thr Gln Ile Pro Leu Val Lys Ala Tyr Gln Ile Ser Ser
465                 470                 475                 480

ggc act act gtg agg aga ggt cca gga ttc aca gga ggc gat ata ctt     1488
Gly Thr Thr Val Arg Arg Gly Pro Gly Phe Thr Gly Gly Asp Ile Leu
                485                 490                 495

cga aga act ggt ccc ggt aca ttt ggg gat ata aaa cta aat atc aat     1536
Arg Arg Thr Gly Pro Gly Thr Phe Gly Asp Ile Lys Leu Asn Ile Asn
```

```
            500                   505                   510

tca cca tta tct caa aga tat cgc gta agg att cgt tat gct tct act      1584
Ser Pro Leu Ser Gln Arg Tyr Arg Val Arg Ile Arg Tyr Ala Ser Thr
        515                   520                   525

act gat tta caa ttt ttc acg aat att aat gga act acc att aat atg      1632
Thr Asp Leu Gln Phe Phe Thr Asn Ile Asn Gly Thr Thr Ile Asn Met
    530                   535                   540

ggt aat ttc cca aaa acc gtg aat aat tcg agt tct gaa ggc tat aga      1680
Gly Asn Phe Pro Lys Thr Val Asn Asn Ser Ser Ser Glu Gly Tyr Arg
545                   550                   555                   560

act gta tca ttt agt act cca ttt agc ttt tca aat gca caa agt ata      1728
Thr Val Ser Phe Ser Thr Pro Phe Ser Phe Ser Asn Ala Gln Ser Ile
                565                   570                   575

ttt aga tta ggt ata caa gct ttt tct gga gtc cac gag att cac gtt      1776
Phe Arg Leu Gly Ile Gln Ala Phe Ser Gly Val His Glu Ile His Val
            580                   585                   590

gat aga att gaa ttt gtc ccg gca gag gta aca ttt gag gca gag tat      1824
Asp Arg Ile Glu Phe Val Pro Ala Glu Val Thr Phe Glu Ala Glu Tyr
        595                   600                   605

gat tta gaa agg gcg caa aag gcg gta aat gca cta ttt aca tct aca      1872
Asp Leu Glu Arg Ala Gln Lys Ala Val Asn Ala Leu Phe Thr Ser Thr
    610                   615                   620

aat cca aaa gat atg aaa aca tat gtg aca gaa tct cag att gac caa      1920
Asn Pro Lys Asp Met Lys Thr Tyr Val Thr Glu Ser Gln Ile Asp Gln
625                   630                   635                   640

gtg ttc aat cta gta gag tgc tta tcg gac gag gtc tgt ctc gat gag      1968
Val Phe Asn Leu Val Glu Cys Leu Ser Asp Glu Val Cys Leu Asp Glu
                645                   650                   655

aag aga gaa tta ttc aag aaa gta aaa tac gcg aag caa ctc aat att      2016
Lys Arg Glu Leu Phe Lys Lys Val Lys Tyr Ala Lys Gln Leu Asn Ile
            660                   665                   670

gag cgt aac atg                                                      2028
Glu Arg Asn Met
        675


<210> SEQ ID NO 2
<211> LENGTH: 676
<212> TYPE: PRT
<213> ORGANISM: Bacillus thuringiensis

<400> SEQUENCE: 2

Met Glu Glu Arg Ser Met Asn Ser Asn Glu His Asp Tyr Leu Lys Val
 1               5                   10                  15

Cys Asp Asp Leu Ser Glu Thr Asn Met Glu Arg Phe Asp Lys Asn Asp
            20                  25                  30

Ala Leu Glu Ile Gly Met Ser Ile Val Ser Glu Leu Leu Gly Met Ile
        35                  40                  45

Pro Gly Gly Ala Ala Leu Gln Phe Val Phe Asn Gln Leu Trp Ser Arg
    50                  55                  60

Leu Gly Asp Ser Gly Trp Ser Ala Phe Met Glu His Val Glu Glu Leu
65                  70                  75                  80

Ile Asp Thr Lys Ile Glu Gly Tyr Ala Lys Asn Lys Ala Leu Ser Glu
                85                  90                  95

Leu Ala Gly Met His Arg Asn Leu Glu Thr Tyr Ile Lys Leu Leu Asn
            100                 105                 110

Glu Trp Glu Asn Asn Thr Gly Ser Ser Lys Ala Gln Gly Arg Val Ala
        115                 120                 125

Asn Tyr Phe Glu Ser Leu Glu Gln Ala Val Glu Arg Gly Met Pro Gln
    130                 135                 140
```

-continued

```
Phe Ala Val Gly Asn Phe Glu Ile Pro Leu Leu Thr Val Tyr Val Gln
145                 150                 155                 160

Ala Ala Asn Leu His Leu Leu Leu Leu Arg Asp Val Ser Val Tyr Gly
                165                 170                 175

Lys Arg Trp Gly Trp Ser Asp Gln Lys Ile Lys Ile Tyr Tyr Glu Lys
            180                 185                 190

Gln Val Lys Tyr Thr His Glu Tyr Thr Asn His Cys Ser Thr Trp Tyr
        195                 200                 205

Asn Arg Gly Leu Asp Lys Leu Lys Asn Lys Gly Ser Ser Tyr Gln Asp
    210                 215                 220

Trp Tyr Asn Tyr Asn Arg Phe Arg Arg Glu Ile Thr Leu Thr Val Leu
225                 230                 235                 240

Asp Ile Val Ala Val Phe Pro His Tyr Asp Val Lys Ala Tyr Pro Ile
                245                 250                 255

Gln Thr Val Gly Gln Leu Thr Arg Glu Val Tyr Thr Asp Pro Leu Ile
            260                 265                 270

Asn Phe Asn Pro Gln Leu Asp Ser Val Ser Gln Leu Pro Thr Phe Ser
        275                 280                 285

Asp Met Glu Asn Ala Thr Ile Arg Thr Pro His Leu Met Glu Phe Leu
    290                 295                 300

Arg Met Leu Thr Ile Tyr Thr Asp Trp Tyr Ser Val Gly Arg Asn Tyr
305                 310                 315                 320

Tyr Trp Gly Gly His Arg Val Thr Ser Tyr Arg Val Gly Gly Glu Asn
                325                 330                 335

Ile Thr Ser Pro Leu Tyr Gly Ser Glu Ala Asn Gln Glu Leu Pro Arg
            340                 345                 350

Gln Leu Tyr Phe Tyr Gly Pro Val Phe Arg Thr Leu Ser Asn Pro Thr
        355                 360                 365

Leu Arg Tyr Leu Gln Gln Pro Ala Pro Ala Pro Pro Phe Ala Leu Arg
    370                 375                 380

Arg Leu Glu Gly Val Glu Phe His Thr Thr Thr Gly Thr Asp Met Tyr
385                 390                 395                 400

Arg Glu Arg Gly Ser Val Asp Ser Phe Asn Glu Leu Pro Pro Phe Asn
                405                 410                 415

Pro Val Gly Leu Pro Arg Asn Ala Tyr Ser His Arg Leu Cys His Ala
            420                 425                 430

Thr Phe Val Arg Lys Ser Gly Thr Pro Tyr Leu Ile Thr Gly Thr Val
        435                 440                 445

Phe Ser Trp Thr His Arg Ser Ala Glu Glu Thr Asn Thr Ile Asp Ser
    450                 455                 460

Asn Arg Ile Thr Gln Ile Pro Leu Val Lys Ala Tyr Gln Ile Ser Ser
465                 470                 475                 480

Gly Thr Thr Val Arg Arg Gly Pro Gly Phe Thr Gly Gly Asp Ile Leu
                485                 490                 495

Arg Arg Thr Gly Pro Gly Thr Phe Gly Asp Ile Lys Leu Asn Ile Asn
            500                 505                 510

Ser Pro Leu Ser Gln Arg Tyr Arg Val Arg Ile Arg Tyr Ala Ser Thr
        515                 520                 525

Thr Asp Leu Gln Phe Phe Thr Asn Ile Asn Gly Thr Thr Ile Asn Met
    530                 535                 540

Gly Asn Phe Pro Lys Thr Val Asn Asn Ser Ser Ser Glu Gly Tyr Arg
545                 550                 555                 560

Thr Val Ser Phe Ser Thr Pro Phe Ser Phe Ser Asn Ala Gln Ser Ile
```

-continued

```
                565                 570                 575

Phe Arg Leu Gly Ile Gln Ala Phe Ser Gly Val His Glu Ile His Val
            580                 585                 590

Asp Arg Ile Glu Phe Val Pro Ala Glu Val Thr Phe Glu Ala Glu Tyr
        595                 600                 605

Asp Leu Glu Arg Ala Gln Lys Ala Val Asn Ala Leu Phe Thr Ser Thr
    610                 615                 620

Asn Pro Lys Asp Met Lys Thr Tyr Val Thr Glu Ser Gln Ile Asp Gln
625                 630                 635                 640

Val Phe Asn Leu Val Glu Cys Leu Ser Asp Glu Val Cys Leu Asp Glu
                645                 650                 655

Lys Arg Glu Leu Phe Lys Lys Val Lys Tyr Ala Lys Gln Leu Asn Ile
            660                 665                 670

Glu Arg Asn Met
        675


<210> SEQ ID NO 3
<211> LENGTH: 2031
<212> TYPE: DNA
<213> ORGANISM: Artificial Sequence
<220> FEATURE:
<223> OTHER INFORMATION: synthetic sequence encoding AXMI-150

<400> SEQUENCE: 3

atggaggaga ggagcatgaa cagcaatgaa catgactacc tcaaggtttg tgatgatctt      60

tcagaaacaa acatggagag atttgacaag aatgatgctc tggagattgg gatgagcatc     120

gtcagcgagc tgctggggat gatccccggc ggcgccgccc tccagtttgt tttcaatcag     180

ctctggagca ggctgggaga ttctggatgg agcgccttca tggagcatgt ggaggagctg     240

atcgacacca agattgaagg atatgccaag aacaaggcgc tctcagagct ggctgggatg     300

cacaggaacc tggagacata catcaagctg ctgaatgaat gggagaacaa cactggaagc     360

tcaaaagctc aaggaagggt ggccaactac tttgagagct tggagcaagc tgtggagaga     420

gggatgccgc agttcgccgt cggcaacttc gagatcccgc tgctcaccgt ctatgttcaa     480

gctgccaacc tccacctgct gctgctgaga gatgtttcag tttatggaaa aagatggggc     540

tggagcgacc agaagatcaa gatctactat gagaagcagg tgaagtacac ccatgagtac     600

accaaccact gctccacctg gtacaacaga gggctggaca agctgaagaa caaaggatca     660

agctaccaag attggtacaa ctacaacagg ttcagaaggg agatcacctt gacggtgctg     720

gacatcgtcg ccgtctttcc tcattatgat gtcaaggcct accccatcca aactgttggc     780

cagctgacaa gggaggtgta cacagatcct ctcatcaact tcaaccccca gctggacagc     840

gtcagccagc tgccaacctt ctcagacatg gagaatgcca ccatcaggac gccgcacctg     900

atggagttct tgaggatgct caccatctac actgattggt actctgttgg aaggaactac     960

tactggggag gccaccgcgt caccagctac agggttggag gagaaaacat cacctcgccg    1020

ctctatggat cagaagcaaa ccaggagctg ccgcggcagc tctacttcta tgggccggtg    1080

ttcagaaccc tctctaatcc aaccttgaga tatctccagc agccggcgcc ggcgccgcca    1140

tttgctctcc gccgcctgga aggagtggag ttccacacca ccaccggcac cgacatgtac    1200

agagaaagag gaagcgtgga ttcattcaat gagctgccgc ccttcaaccc tgttgggctg    1260

ccaagaaatg cctacagcca ccgcctctgc catgccacct tcgtgaggaa gagcggcacc    1320

ccctacctca tcaccggcac cgtgttcagc tggacccacc gctctgctga agaaacaaac    1380

accatcgaca gcaacaggat cacccagatc ccgctggtga aggcctacca gatctcctca    1440
```

ggcaccaccg tccgccgcgg ccctggcttc actggaggag acatcttgag aagaactgga 1500
cctggcacct tcggcgacat caagctcaac atcaactcgc cgctctccca aagatacagg 1560
gtgaggatca gatatgcttc aacaactgat cttcagttct tcaccaacat caatggcacc 1620
accatcaaca tgggcaactt cccaaaaact gtcaacaaca gcagctcaga aggctacagg 1680
acggtgagct tctccacccc cttctccttc agcaatgctc aaagcatctt ccgcctcggc 1740
atccaggcct tctccggcgt ccatgagatc catgtggaca ggattgaatt tgttcctgct 1800
gaagtcacct ttgaagcaga atatgatctg gagagggcgc agaaggccgt caatgctctc 1860
ttcacctcaa caaaccccaa ggacatgaaa acatatgtca cagaaagcca gattgatcaa 1920
gttttcaacc tggtggagtg cctctctgat gaagtttgct tggatgagaa gagggagctg 1980
ttcaagaagg tgaaatatgc caagcagctc aacatcgaga ggaacatgtg a 2031

<210> SEQ ID NO 4
<211> LENGTH: 2031
<212> TYPE: DNA
<213> ORGANISM: Artificial Sequence
<220> FEATURE:
<223> OTHER INFORMATION: synthetic sequence encoding AXMI-150

<400> SEQUENCE: 4
atggaggaga ggagcatgaa cagcaatgaa catgactacc tcaaggtttg tgatgatctt 60
tcagaaacaa acatggagag atttgacaag aatgatgctc tggagattgg gatgagcatc 120
gtcagcgagc tgctggggat gatccccggc ggcgccgccc tccagtttgt tttcaatcag 180
ctctggagca ggctgggaga ttctggatgg agcgccttca tggagcatgt ggaggagctg 240
atcgacacca agattgaagg atatgccaag aacaaggcgc tctcagagct ggctgggatg 300
cacaggaacc tggagacata catcaagctg ctgaatgaat gggagaacaa cactggaagc 360
tcaaaagctc aaggaagggt ggccaactac tttgagagct tggagcaagc tgtggagaga 420
gggatgccgc agttcgccgt cggcaacttc gagatcccgc tgctcaccgt ctatgttcaa 480
gctgccaacc tccacctgct gctgctgaga gatgtttcag tttatggaaa aagatggggc 540
tggagcgacc agaagatcaa gatctactat gagaagcagg tgaagtacac ccatgagtac 600
accaaccact gctccacctg gtacaacaga gggctggaca agctgaagaa caaaggatca 660
agctaccaag attggtacaa ctacaacagg ttcagaaggg agatcacctt gacggtgctg 720
gacatcgtcg ccgtctttcc tcattatgat gtcaaggcct accccatcca aactgttggc 780
cagctgacaa gggaggtgta cacagatcct ctcatcaact tcaaccccca gctggacagc 840
gtcagccagc tgccaacctt ctcagacatg gagaatgcca ccatcaggac gccgcacctg 900
atggagttct tgaggatgct caccatctac actgattggt actctgttgg aaggaactac 960
tactggggag gccaccgcgt caccagctac agggttggag gagaaaacat cacctcgccg 1020
ctctatggat cagaagcaaa ccaggagctg ccgcggcagc tctacttcta tgggccggtg 1080
ttcagaaccc tctctaatcc aaccttgaga tatctccagc agccggcgcc ggcgccgcca 1140
tttgctctcc gccgcctgga aggagtggag ttccacacca ccaccggcac cgacatgtac 1200
agagaaagag gaagcgtgga ttcattcaat gagctgccgc ccttcaaccc tgttgggctg 1260
ccaagaaatg cctacagcca ccgcctctgc catgccacct tcgtgaggaa gagcggcacc 1320
ccctacctca tcaccggcac cgtgttcagc tggacccacc gctctgctga agaaacaaac 1380
accatcgaca gcaacaggat cacccagatc ccgctggtga aggcctacca gatctcctca 1440
ggcaccaccg tccgccgcgg ccctggcttc actggaggag acatcttgag aagaactgga 1500

```
cctggcacct tcggcgacat caagctcaac atcaactcgc cgctctccca aagatacagg   1560

gtgaggatca gatatgcttc aacaactgat cttcagttct tcaccaacat caatggcacc   1620

accatcaaca tgggcaactt cccaaaaact gtcaacaaca gcagctcaga aggctacagg   1680

acggtgagct tctccacccc cttctccttc agcaatgctc aaagcatctt ccgcctcggc   1740

atccaggcct tctccggcgt ccatgagatc catgtggaca ggattgaatt tgttcctgct   1800

gaagtcacct ttgaagcaga atatgatctg gagagggcgc agaaggccgt caatgctcta   1860

tttacctcaa caaaccccaa ggacatgaaa acatatgtca cagaaagcca gattgatcaa   1920

gttttcaacc tggtggagtg cctctctgat gaagtttgct tggatgagaa gagggagctg   1980

ttcaagaagg tgaaatatgc caagcagctc aacatcgaga ggaacatgtg a            2031
```

```
<210> SEQ ID NO 5
<211> LENGTH: 2028
<212> TYPE: DNA
<213> ORGANISM: Artificial Sequence
<220> FEATURE:
<223> OTHER INFORMATION: synthetic sequence encoding AXMI-150

<400> SEQUENCE: 5

atggaggaga ggagcatgaa cagcaatgaa catgactacc tcaaggtttg tgatgatctt     60

tcagaaacaa acatggagag atttgacaag aatgatgctc tggagattgg gatgagcatc    120

gtcagcgagc tgctggggat gatccccggc ggcgccgccc tccagtttgt tttcaatcag    180

ctctggagca ggctgggaga ttctggatgg agcgccttca tggagcatgt ggaggagctg    240

atcgacacca agattgaagg atatgccaag aacaaggcgc tctcagagct ggctgggatg    300

cacaggaacc tggagacata catcaagctg ctgaatgaat gggagaacaa cactggaagc    360

tcaaaagctc aaggaagggt ggccaactac tttgagagct tggagcaagc tgtggagaga    420

gggatgccgc agttcgccgt cggcaacttc gagatcccgc tgctcaccgt ctatgttcaa    480

gctgccaacc tccacctgct gctgctgaga gatgtttcag tttatggaaa aagatggggc    540

tggagcgacc agaagatcaa gatctactat gagaagcagg tgaagtacac ccatgagtac    600

accaaccact gctccacctg gtacaacaga gggctggaca agctgaagaa caaaggatca    660

agctaccaag attggtacaa ctacaacagg ttcagaaggg agatcacctt gacggtgctg    720

gacatcgtcg ccgtctttcc tcattatgat gtcaaggcct accccatcca aactgttggc    780

cagctgacaa gggaggtgta cacagatcct ctcatcaact tcaacccccca gctggacagc    840

gtcagccagc tgccaacctt ctcagacatg gagaatgcca ccatcaggac gccgcacctg    900

atggagttct tgaggatgct caccatctac actgattggt actctgttgg aaggaactac    960

tactggggag gccaccgcgt caccagctac agggttggag gagaaaacat cacctcgccg   1020

ctctatggat cagaagcaaa ccaggagctg ccgcggcagc tctacttcta tgggccggtg   1080

ttcagaaccc tctctaatcc aaccttgaga tatctccagc agccggcgcc ggcgccgcca   1140

tttgctctcc gccgcctgga aggagtggag ttccacacca ccaccggcac cgacatgtac   1200

agagaaagag gaagcgtgga ttcattcaat gagctgccgc ccttcaaccc tgttgggctg   1260

ccaagaaatg cctacagcca ccgcctctgc catgccacct tcgtgaggaa gagcggcacc   1320

ccctacctca tcaccggcac cgtgttcagc tggacccacc gctctgctga agaaacaaac   1380

accatcgaca gcaacaggat cacccagatc ccgctggtga aggcctacca gatctcctca   1440

ggcaccaccg tccgccgcgg ccctggcttc actggaggag acatcttgag aagaactgga   1500

cctggcacct tcggcgacat caagctcaac atcaactcgc cgctctccca aagatacagg   1560
```

gtgaggatca gatatgcttc aacaactgat cttcagttct tcaccaacat caatggcacc 1620
accatcaaca tgggcaactt cccaaaaact gtcaacaaca gcagctcaga aggctacagg 1680
acggtgagct tctccacccc cttctccttc agcaatgctc aaagcatctt ccgcctcggc 1740
atccaggcct tctccggcgt ccatgagatc catgtggaca ggattgaatt tgttcctgct 1800
gaagtcacct ttgaagcaga atatgatctg gagagggcgc agaaggccgt caatgctctc 1860
ttcacctcaa caaaccccaa ggacatgaaa acatatgtca cagaaagcca gattgatcaa 1920
gttttcaacc tggtggagtg cctctctgat gaagtttgct tggatgagaa gagggagctg 1980
ttcaagaagg tgaaatatgc caagcagctc aacatcgaga ggaacatg 2028

<210> SEQ ID NO 6
<211> LENGTH: 2028
<212> TYPE: DNA
<213> ORGANISM: Artificial Sequence
<220> FEATURE:
<223> OTHER INFORMATION: synthetic sequence encoding AXMI-150

<400> SEQUENCE: 6
atggaggaga ggagcatgaa cagcaatgaa catgactacc tcaaggtttg tgatgatctt 60
tcagaaacaa acatggagag atttgacaag aatgatgctc tggagattgg gatgagcatc 120
gtcagcgagc tgctggggat gatccccggc ggcgccgccc tccagtttgt tttcaatcag 180
ctctggagca ggctgggaga ttctggatgg agcgccttca tggagcatgt ggaggagctg 240
atcgacacca agattgaagg atatgccaag aacaaggcgc tctcagagct ggctgggatg 300
cacaggaacc tggagacata catcaagctg ctgaatgaat gggagaacaa cactggaagc 360
tcaaaagctc aaggaagggt ggccaactac tttgagagct tggagcaagc tgtggagaga 420
gggatgccgc agttcgccgt cggcaacttc gagatcccgc tgctcaccgt ctatgttcaa 480
gctgccaacc tccacctgct gctgctgaga gatgtttcag tttatggaaa aagatggggc 540
tggagcgacc agaagatcaa gatttattat gaaaagcagg tgaagtacac ccatgagtac 600
accaaccact gctccacctg gtacaacaga gggctggaca agctgaagaa caaaggatca 660
agctaccaag attggtacaa ctacaacagg ttcagaaggg agatcacctt gacggtgctg 720
gacatcgtcg ccgtctttcc tcattatgat gtcaaggcct accccatcca aactgttggc 780
cagctgacaa gggaggtgta cacagatcct ctcatcaact tcaacccccca gctggacagc 840 gtcagccagc tgccaacctt ctcagacatg gagaatgcca ccatcaggac gccgcacctg 900
atggagttct tgaggatgct caccatctac actgattggt actctgttgg aaggaactac 960
tactggggag gccaccgcgt caccagctac agggttggag gagaaaacat cacctcgccg 1020
ctctatggat cagaagcaaa ccaggagctg ccgcggcagc tctacttcta tgggccggtg 1080
ttcagaaccc tctctaatcc aaccttgaga tatctccagc agccggcgcc ggcgccgcca 1140
tttgctctcc gccgcctgga aggagtggag ttccacacca ccaccggcac cgacatgtac 1200
agagaaagag gaagcgtgga ttcattcaat gagctgccgc ccttcaaccc tgttgggctg 1260
ccaagaaatg cctacagcca ccgcctctgc catgccacct tcgtgaggaa gagcggcacc 1320
ccctacctca tcaccggcac cgtgttcagc tggacccacc gctctgctga agaaacaaac 1380
accatcgaca gcaacaggat cacccagatc ccgctggtga aggcctacca gatctcctca 1440
ggcaccaccg tccgccgcgg ccctggcttc actggaggag acatcttgag aagaactgga 1500
cctggcacct tcggcgacat caagctcaac atcaactcgc cgctctccca aagatacagg 1560
gtgaggatca gatatgcttc aacaactgat cttcagttct tcaccaacat caatggcacc 1620
accatcaaca tgggcaactt cccaaaaact gtcaacaaca gcagctcaga aggctacagg 1680
acggtgagct tctccacccc cttctccttc agcaatgctc aaagcatctt ccgcctcggc 1740
atccaggcct tctccggcgt ccatgagatc catgtggaca ggattgaatt tgttcctgct 1800
gaagtcacct ttgaagcaga atatgatctg gagagggcgc agaaggccgt caatgctctc 1860
ttcacctcaa caaaccccaa ggacatgaaa acatatgtca cagaaagcca gattgatcaa 1920
gttttcaacc tggtggagtg cctctctgat gaagtttgct tggatgagaa gagggagctg 1980
ttcaagaagg tgaaatatgc caagcagctc aacatcgaga ggaacatg 2028

<210> SEQ ID NO 7
<211> LENGTH: 2028
<212> TYPE: DNA
<213> ORGANISM: Artificial Sequence
<220> FEATURE:
<223> OTHER INFORMATION: synthetic sequence encoding AXMI-150

<400> SEQUENCE: 7
atggaggaga ggagcatgaa cagcaatgaa catgactacc tcaaggtttg tgatgatctt 60
tcagaaacaa acatggagag atttgacaag aatgatgctc tggagattgg gatgagcatc 120
gtcagcgagc tgctggggat gatccccggc ggcgccgccc tccagtttgt tttcaatcag 180
ctctggagca ggctgggaga ttctggatgg agcgccttca tggagcatgt ggaggagctg 240
atcgacacca agattgaagg atatgccaag aacaaggcgc tctcagagct ggctgggatg 300
cacaggaacc tggagacata catcaagctg ctgaatgaat gggagaacaa cactggaagc 360
tcaaaagctc aaggaagggt ggccaactac tttgagagct tggagcaagc tgtggagaga 420
gggatgccgc agttcgccgt cggcaacttc gagatcccgc tgctcaccgt ctatgttcaa 480
gctgccaacc tccacctgct gctgctgaga gatgtttcag tttatggaaa aagatggggc 540
tggagcgacc agaagatcaa gatctactat gagaagcagg tgaagtacac ccatgagtac 600
accaaccact gctccacctg gtacaacaga gggctggaca agctgaagaa caaaggatca 660
agctaccaag attggtacaa ctacaacagg ttcagaaggg agatcacctt gacggtgctg 720
gacatcgtcg ccgtctttcc tcattatgat gtcaaggcct accccatcca aactgttggc 780
cagctgacaa gggaggtgta cacagatcct ctcatcaact tcaaccccca gctggacagc 840
gtcagccagc tgccaacctt ctcagacatg gagaatgcca ccatcaggac gccgcacctg 900
atggagttct tgaggatgct caccatctac actgattggt actctgttgg aaggaactac 960
tactggggag gccaccgcgt caccagctac agggttggag gagaaaacat cacctcgccg 1020
ctctatggat cagaagcaaa ccaggagctg ccgcggcagc tctacttcta tgggccggtg 1080
ttcagaaccc tctctaatcc aaccttgaga tatctccagc agccggcgcc ggcgccgcca 1140
tttgctctcc gccgcctgga aggagtggag ttccacacca ccaccggcac cgacatgtac 1200
agagaaagag gaagcgtgga ttcattcaat gagctgccgc ccttcaaccc tgttgggctg 1260
ccaagaaatg cctacagcca ccgcctctgc catgccacct tcgtgaggaa gagcggcacc 1320
ccctacctca tcaccggcac cgtgttcagc tggacccacc gctctgctga agaaacaaac 1380
accatcgaca gcaacaggat cacccagatc ccgctggtga aggcctacca gatctcctca 1440
ggcaccaccg tccgccgcgg ccctggcttc actggaggag acatcttgag aagaactgga 1500
cctggcacct tcggcgacat caagctcaac atcaactcgc cgctctccca aagatacagg 1560
gtgaggatca gatatgcttc aacaactgat cttcagttct tcaccaacat caatggcacc 1620
accatcaaca tgggcaactt cccaaaaact gtcaacaaca gcagctcaga aggctacagg 1680
acggtgagct tctccacccc cttctccttc agcaatgctc aaagcatctt ccgcctcggc 1740
atccaggcct tctccggcgt ccatgagatc catgtggaca ggattgaatt tgttcctgct 1800
gaagtcacct ttgaagcaga atatgatctg gagagggcgc agaaggccgt caatgctcta 1860
tttacctcaa caaaccccaa ggacatgaaa acatatgtca cagaaagcca gattgatcaa 1920
gttttcaacc tggtggagtg cctctctgat gaagtttgct tggatgagaa gagggagctg 1980
ttcaagaagg tgaaatatgc caagcagctc aacatcgaga ggaacatg 2028

<210> SEQ ID NO 8
<211> LENGTH: 1806
<212> TYPE: DNA
<213> ORGANISM: Artificial Sequence
<220> FEATURE:
<223> OTHER INFORMATION: synthetic sequence encoding axmi-004

<400> SEQUENCE: 8
atgaacagca aggagcatga ctacctcaag gtctgcaatg atctttctga tgccaacatc 60
aacatggaga gatttgacaa gaatgatgct ctggagattg ggatgagcat cgtcagcgag 120
ctgattggga tgatccctgg aggcacggcg ctgcaatttg ttttcaatca gctctggagc 180
aggctgggag actcaggatg gaatgccttc atggagcatg tggaggagct catcgacacc 240
aagattgaag gatatgccaa gaacaaggcg ctctccgagc tggctggcat ccagaggaac 300
ctggagacat acatccagct gagaaatgaa tgggagaatg acatcgagaa cagcaaggct 360
caaggaaagg tggccaacta ctatgagagc ttggagcaag ctgtggagag atcaatgccg 420
cagttcgccg tggagaactt cgaggtgccg ctgctcaccg tctatgttca agctgccaac 480
ctccatctgc tgctgctgag agatgtttct gtttatggaa aatgctgggg ctggagcgag 540
cagaagatca agatttatta tgataagcag atcaagtaca cccatgagta caccaaccac 600
tgcgtcaact ggtacaacaa ggggctagag aggctgaaga acaaaggaag cagctaccaa 660
gattggtaca actacaacag gttcagaagg gagatgaccc tcaccgtgct ggacattgtt 720
gctctcttcc ctcattatga tgttcaaaca tatcccatca ccactgttgc tcagctgaca 780
agagaagtct acacagatcc tcttctcaac ttcaatccaa agctacattc tgtttctcag 840
cttccttcct tctctgacat ggaaaatgca accatcagga cgcctcattt gatggagttc 900
ttgaggatgc tcaccatcta cacagattgg tattcagttg gaagaaacta ctactgggga 960
ggacaccgcg tcacaagcta tcatgttgga ggtgaaaaca tcagatctcc tctttatgga 1020
agagaagcaa atcaagaagt tccaagagat ttctacttct atggacctgt gttcaaaaca 1080
ttgagcaagc caacattgag gcctcttcag cagccggcgc cggcgcctcc tttcaacttg 1140
agatcattgg aaggagtgga gttccacaca ccaactggca gcttcatgta cagagaaaga 1200
ggatctgttg acagcttcaa tgagcttcct ccccttcaatc ctgttggcct tcctcacaag 1260
gtttacagcc accgcctctg ccatgcaaca tttgtgagga agagcggcac gccatatctc 1320
accaccggcg ccatcttcag ctggacccac cgctcagcag aagaaacaaa caccattgaa 1380
agcaacatca tcacccagat tcctctggtg aaggcctacc aaattggaag cggcaccacc 1440
gtcagaaaag gacctggctt cactggagga gatatcttga gaagaactgg acctggaaca 1500
tttggagaca tgaggatcaa catcaatgct cctctctctc aaagatacag ggtgaggatc 1560
agatatgctt caacaactga tcttcaattt gtcacctcca tcaatggcac caccatcaac 1620
attggaaact tcccaaaaac catcaacaac ctcaacaccc ttggatcaga aggatacagg 1680
acagtgagct tctccacccc cttctccttc agcaatgctc aaagcatctt cagattgggc 1740
atccaagcct tctccggcgt ccaagaagtt tatgttgaca agattgagtt catccctgtg 1800
gaataa 1806

<210> SEQ ID NO 9
<211> LENGTH: 1806
<212> TYPE: DNA
<213> ORGANISM: Artificial Sequence
<220> FEATURE:
<223> OTHER INFORMATION: synthetic sequence encoding axmi-004

<400> SEQUENCE: 9
atgaactcca aggagcacga ctacctcaag gtgtgcaacg acctctctga cgccaacatc 60
aacatggagc gcttcgacaa gaacgacgcc ctcgagatcg gcatgtcaat cgtgtccgag 120
ctcatcggca tgatcccggg cggcaccgcc cttcagttcg tgttcaacca gctctggtcc 180
cgcctcggcg actccggctg gaacgccttc atggagcacg tggaggagct catcgacacc 240
aagatcgagg gctacgctaa gaacaaggcc ctctcagagc tcgccggcat ccagcgcaac 300
ctcgagacct acatccagct ccgcaacgag tgggagaacg acatagagaa ctccaaggcc 360
cagggcaagg tggccaacta ctacgagtcc ctcgagcagg ccgtggagcg ctccatgccg 420
cagttcgccg tggagaactt cgaggtgccg ttactcaccg tgtacgtgca agccgctaac 480
ctccacctcc tcctcctccg cgacgtgtcc gtgtacggca agtgctgggg ctggtccgag 540
cagaagataa agatctacta cgacaagcag atcaagtaca cccacgagta caccaaccac 600
tgcgtgaact ggtacaacaa gggcctcgag cgcctcaaga acaagggctc atcctaccag 660
gactggtaca actacaaccg cttccgtagg gagatgaccc tcaccgtgct cgacatcgtg 720
gccctcttcc cgcactacga cgtgcagacc tacccgatca ccaccgtggc ccagttaacc 780
cgcgaggtgt acaccgaccc gctcctcaac ttcaacccga agctccactc cgtgtcccag 840
ctcccgtcct tctccgacat ggagaacgcc accatccgca ccccgcacct catggagttc 900
cttaggatgc tcaccatcta caccgactgg tactccgtgg gccgcaacta ctactggggc 960
ggccaccgcg tgacctcata ccacgtgggc ggtgagaaca tccgctcccc gctctacggc 1020
cgcgaggcca accaggaggt gccgcgcgac ttctacttct acggcccggt gttcaagacc 1080
ctctccaagc cgaccctccg cccgctccag cagccggccc cggccccgcc gtttaacctc 1140
cgctccttag agggcgtgga gttccacacc ccgaccggct cattcatgta ccgcgagcgc 1200
ggctccgtag actccttcaa tgagctcccg ccgttcaacc cggtgggcct cccgcacaag 1260
gtgtactctc accgcctctg ccacgccacc ttcgtgcgca agtccggcac cccgtacctc 1320
accaccggcg ccatcttctc ctggacccac cgctccgctg aggagaccaa caccatcgag 1380
tcaaacatca tcacccagat cccgctcgtg aaggcctacc agatcggctc cggcaccacc 1440
gtgcgcaagg gcccgggctt caccggcggc gacatcctcc gccgcaccgg cccgggcacc 1500
ttcggcgaca tgcgcatcaa catcaacgcc ccgctctccc agcgctaccg cgtgcgcatc 1560
cgctacgcta gcaccaccga cctccagttc gtgacctcaa tcaacggcac caccatcaac 1620
atcggcaact tcccgaagac catcaacaac ctcaacaccc tcggctccga gggctaccgc 1680
accgtgagct tctccacccc gttctccttc tccaacgccc agtccatctt ccgcctcggc 1740
atccaggcct tctccggcgt gcaagaggtg tacgtggaca agattgagtt catcccggtg 1800
gagtga 1806

<210> SEQ ID NO 10
<211> LENGTH: 1743

-continued

<212> TYPE: DNA
<213> ORGANISM: Artificial Sequence
<220> FEATURE:
<223> OTHER INFORMATION: synthetic sequence encoding axmi-004

<400> SEQUENCE: 10
atggagcgct tcgacaagaa cgacgccctc gagatcggca tgtcaatcgt gtccgagctc 60
atcggcatga tcccgggcgg caccgccctt cagttcgtgt tcaaccagct ctggtcccgc 120
ctcggcgact ccggctggaa cgccttcatg gagcacgtgg aggagctcat cgacaccaag 180
atcgagggct acgctaagaa caaggccctc tcagagctcg ccggcatcca gcgcaacctc 240
gagacctaca tccagctccg caacgagtgg gagaacgaca tagagaactc caaggcccag 300
ggcaaggtgg ccaactacta cgagtccctc gagcaggccg tggagcgctc catgccgcag 360
ttcgccgtgg agaacttcga ggtgccgtta ctcaccgtgt acgtgcaagc cgctaacctc 420
cacctcctcc tcctccgcga cgtgtccgtg tacggcaagt gctggggctg gtccgagcag 480
aagataaaga tctactacga caagcagatc aagtacaccc acgagtacac caaccactgc 540
gtgaactggt acaacaaggg cctcgagcgc ctcaagaaca agggctcatc ctaccaggac 600
tggtacaact acaaccgctt ccgtagggag atgaccctca ccgtgctcga catcgtggcc 660
ctcttcccgc actacgacgt gcagacctac ccgatcacca ccgtggccca gttaacccgc 720
gaggtgtaca ccgacccgct cctcaacttc aacccgaagc tccactccgt gtcccagctc 780
ccgtccttct ccgacatgga gaacgccacc atccgcaccc cgcacctcat ggagttcctt 840
aggatgctca ccatctacac cgactggtac tccgtgggcc gcaactacta ctggggcggc 900
caccgcgtga cctcatacca cgtgggcggt gagaacatcc gctccccgct ctacggccgc 960
gaggccaacc aggaggtgcc gcgcgacttc tacttctacg gcccggtgtt caagaccctc 1020
tccaagccga ccctccgccc gctccagcag ccggccccgg ccccgccgtt taacctccgc 1080
tccttagagg gcgtggagtt ccacaccccg accggctcat tcatgtaccg cgagcgcggc 1140
tccgtagact ccttcaatga gctcccgccg ttcaacccgg tgggcctccc gcacaaggtg 1200
tactctcacc gcctctgcca cgccaccttc gtgcgcaagt ccggcacccc gtacctcacc 1260
accggcgcca tcttctcctg gacccaccgc tccgctgagg agaccaacac catcgagtca 1320
aacatcatca cccagatccc gctcgtgaag gcctaccaga tcggctccgg caccaccgtg 1380
cgcaagggcc cgggcttcac cggcggcgac atcctccgcc gcaccggccc gggcaccttc 1440
ggcgacatgc gcatcaacat caacgccccg ctctcccagc gctaccgcgt gcgcatccgc 1500
tacgctagca ccaccgacct ccagttcgtg acctcaatca acggcaccac catcaacatc 1560
ggcaacttcc cgaagaccat caacaacctc aacaccctcg gctccgaggg ctaccgcacc 1620
gtgagcttct ccaccccgtt ctccttctcc aacgcccagt ccatcttccg cctcggcatc 1680
caggccttct ccggcgtgca agaggtgtac gtggacaaga ttgagttcat cccggtggag 1740
tga 1743

<210> SEQ ID NO 11
<211> LENGTH: 1890
<212> TYPE: DNA
<213> ORGANISM: Artificial Sequence
<220> FEATURE:
<223> OTHER INFORMATION: synthetic sequence encoding axmi-004

<400> SEQUENCE: 11
atgagcgagc tgaagggcaa gttcaagaag agcaccaaca ggacctgctg cttgctgaag 60
atcatcaaca ttggaggaag agggatgaac agcaaggagc atgactacct caaggtgtgc 120

```
aacgacctct cagatgccaa catcaacatg gagagatttg acaagaatga tgctctggag    180
attgggatga gcatcgtctc cgagctgatt gggatgattc ctggagggac ggcgctgcaa    240
tttgtcttca atcagctgtg gtcaaggctg ggagattctg gatggaatgc cttcatggag    300
catgtggagg agctcatcga caccaagatt gaaggatatg ccaagaacaa ggcgctctca    360
gagctggccg gcatccagag gaacctggag acctacatcc agctgaggaa tgaatgggag    420
aatgacatcg agaacagcaa ggctcaaggc aaggtggcca actactacga gagcttggag    480
caagctgttg aaagatcaat gcctcaattt gctgtggaga acttcgaggt gccgctgctc    540
accgtctatg ttcaagctgc caacctccac ctgctgctgc tgagagatgt ttcagtttat    600
ggaaaatgct ggggctggag cgagcagaag atcaagatct actacgacaa gcagatcaag    660
tacacccatg agtacaccaa ccactgcgtc aactggtaca acaaggggct ggagaggctg    720
aagaacaagg gctcaagcta ccaagattgg tacaactaca acaggttcag aagggagatg    780
acattgacgg tgctggacat cgtggcgctc ttccctcatt atgatgttca aacctacccc    840
atcaccaccg tggcgcagct gacaagagaa gtctacaccg acccgctgct aaacttcaac    900
cccaagctgc attctgtgag ccagctgccg agcttctccg acatggagaa tgccaccatc    960
aggacgccgc acctgatgga gttcttgagg atgctcacca tctacactga ttggtattct   1020
gttggaagga actactactg ggcggccac cgcgtcacct catatcatgt tggtggtgag   1080
aacatccgct cgccgctcta tggaagagaa gcaaatcaag aagttccaag agatttctac   1140
ttctatggac ctgtcttcaa gaccttgtca aagccaacat tgaggccgct ccagcagccg   1200
gcgccggcgc cgcccttcaa cctgaggagc ttggaaggag ttgagttcca cacgccaact   1260
ggcagcttca tgtacagaga aagaggatca gtggacagct tcaacgagct gccgcccttc   1320
aaccctgttg ggctgccgca caaggtctac agccaccgcc tctgccatgc caccttcgtg   1380
aggaagagcg gcacgccgta cctcaccacc ggcgccatct tctcatggac ccaccgctct   1440
gctgaagaaa ccaacaccat cgagagcaac atcatcaccc agatcccgct ggtgaaggcc   1500
taccagattg gatcaggcac caccgtgagg aaaggacctg gcttcactgg aggagacatc   1560
ttgaggagga ctggacctgg aacatttgga gacatgagga tcaacatcaa cgcgccgctg   1620
agccaaagat acagggtgag gatcagatat gcttcaacaa ctgatcttca atttgtgaca   1680
agcatcaatg gcaccaccat caacatcggc aacttcccca agaccatcaa caacctcaac   1740
accttgggct cagaaggcta caggacggtg agcttctcca cgcccttcag cttcagcaat   1800
gctcaaagca tcttccgcct cggcatccaa gccttctctg gagttcaaga agtttatgtg   1860
gacaagattg agttcatccc ggtggagtaa                                     1890
```

<210> SEQ ID NO 12
<211> LENGTH: 1890
<212> TYPE: DNA
<213> ORGANISM: Artificial Sequence
<220> FEATURE:
<223> OTHER INFORMATION: synthetic sequence encoding axmi-004

<400> SEQUENCE: 12

```
atgagcgagc tgaagggcaa gttcaagaag agcaccaaca ggacatgctg cttgctgaag     60
atcatcaaca ttggaggaag aggaatgaac agcaaggagc atgactacct caaggtttgc    120
aatgatcttt cagatgccaa catcaacatg gaaagatttg acaagaatga tgctctggag    180
attgggatga gcatcgtctc cgagctgatt gggatgattc ctggaggaac ggcgctgcaa    240
tttgtcttca atcagctgtg gtcaaggctt ggagattctg gatggaatgc cttcatggag    300
```

catgtggagg agctcatcga caccaagatt gaaggatatg ccaagaacaa ggcgctctca 360
gagctggctg gcatccaaag aaatttggag acctacatcc agctgagaaa tgaatgggaa 420
aatgacattg agaacagcaa ggctcaagga aaggtggcca actactatga gagcttggag 480
caagctgttg aaagatcaat gcctcaattt gctgtggaga acttcgaggt gccgctgctc 540
accgtctatg ttcaagctgc caacctccac ctgctgctgc tgagagatgt ttcagtttat 600
ggaaaatgct ggggatggag cgagcagaag atcaagatct actacgacaa gcagatcaag 660
tacactcatg agtacaccaa ccattgtgtc aactggtaca acaaaggact ggagaggctg 720
aagaacaaag gatcaagcta ccaagattgg tacaactaca acagattcag aagagagatg 780
acattgacag tgctggacat tgtggcgctc tttcctcatt atgatgttca aacctacccc 840
atcaccaccg tggcgcagct gacaagagaa gtctacaccg acccgctgct aaacttcaac 900
cccaagctgc attctgtgag ccagctgcca tccttctccg acatggaaaa tgccaccatc 960
aggacgccgc acctgatgga gttcttgagg atgctcacca tctacactga ttggtattct 1020
gttggaagaa actactactg ggcggccac cgcgtgacat catatcatgt tggtggtgaa 1080
aacatcagat cgccgctcta tggaagagaa gcaaatcaag aagttccaag agatttctac 1140
ttctatggac ctgtcttcaa gacattgtca aagccaacat tgaggccgct ccagcagccg 1200
gcgccggcgc cgccattcaa cttgaggagc ttggaaggag ttgagttcca cacaccaact 1260
ggcagcttca tgtacagaga aagaggatca gtggacagct tcaatgagct gccgccattc 1320
aaccctgttg ggcttcctca caaggtctac agccaccgcc tctgccatgc aaccttcgtg 1380
aggaagagcg gcacgccgta cctcaccacc ggcgccatct tctcatggac ccaccgctct 1440
gctgaagaaa caaacaccat cgagagcaac atcatcaccc agatcccgct ggtgaaggcc 1500
taccaaattg gatcaggaac aacagtgagg aaaggacctg gcttcactgg aggagacatc 1560
ttgagaagaa ctggacctgg aacatttgga gacatgagga tcaacatcaa cgcgccgctg 1620
agccaaagat acagggtgag gatcagatat gcttcaacaa ctgatcttca atttgtgaca 1680
agcatcaatg gcaccaccat caacatcggc aacttcccca agaccatcaa caacctcaac 1740
accttgggct cagaaggcta caggacggtg agcttctcca cgccattcag cttctcaaat 1800
gctcaaagca tcttccgcct cggcatccaa gccttctctg gagttcaaga agtttatgtg 1860
gacaagattg agttcatccc ggtggaataa 1890

<210> SEQ ID NO 13
<211> LENGTH: 4
<212> TYPE: PRT
<213> ORGANISM: Artificial Sequence
<220> FEATURE:
<223> OTHER INFORMATION: ER targeting peptide

<400> SEQUENCE: 13

Lys Asp Glu Leu
1

<210> SEQ ID NO 14
<211> LENGTH: 601
<212> TYPE: PRT
<213> ORGANISM: Bacillus thuringiensis

<400> SEQUENCE: 14

Met Asn Ser Lys Glu His Asp Tyr Leu Lys Val Cys Asn Asp Leu Ser
1 5 10 15

Asp Ala Asn Ile Asn Met Glu Arg Phe Asp Lys Asn Asp Ala Leu Glu

-continued

```
            20                  25                  30

Ile Gly Met Ser Ile Val Ser Glu Leu Ile Gly Met Ile Pro Gly Gly
        35                  40                  45

Thr Ala Leu Gln Phe Val Phe Asn Gln Leu Trp Ser Arg Leu Gly Asp
    50                  55                  60

Ser Gly Trp Asn Ala Phe Met Glu His Val Glu Glu Leu Ile Asp Thr
65                  70                  75                  80

Lys Ile Glu Gly Tyr Ala Lys Asn Lys Ala Leu Ser Glu Leu Ala Gly
                85                  90                  95

Ile Gln Arg Asn Leu Glu Thr Tyr Ile Gln Leu Arg Asn Glu Trp Glu
            100                 105                 110

Asn Asp Ile Glu Asn Ser Lys Ala Gln Gly Lys Val Ala Asn Tyr Tyr
        115                 120                 125

Glu Ser Leu Glu Gln Ala Val Glu Arg Ser Met Pro Gln Phe Ala Val
    130                 135                 140

Glu Asn Phe Glu Val Pro Leu Leu Thr Val Tyr Val Gln Ala Ala Asn
145                 150                 155                 160

Leu His Leu Leu Leu Leu Arg Asp Val Ser Val Tyr Gly Lys Cys Trp
                165                 170                 175

Gly Trp Ser Glu Gln Lys Ile Lys Ile Tyr Tyr Asp Lys Gln Ile Lys
            180                 185                 190

Tyr Thr His Glu Tyr Thr Asn His Cys Val Asn Trp Tyr Asn Lys Gly
        195                 200                 205

Leu Glu Arg Leu Lys Asn Lys Gly Ser Ser Tyr Gln Asp Trp Tyr Asn
    210                 215                 220

Tyr Asn Arg Phe Arg Arg Glu Met Thr Leu Thr Val Leu Asp Ile Val
225                 230                 235                 240

Ala Leu Phe Pro His Tyr Asp Val Gln Thr Tyr Pro Ile Thr Thr Val
                245                 250                 255

Ala Gln Leu Thr Arg Glu Val Tyr Thr Asp Pro Leu Leu Asn Phe Asn
            260                 265                 270

Pro Lys Leu His Ser Val Ser Gln Leu Pro Ser Phe Ser Asp Met Glu
        275                 280                 285

Asn Ala Thr Ile Arg Thr Pro His Leu Met Glu Phe Leu Arg Met Leu
    290                 295                 300

Thr Ile Tyr Thr Asp Trp Tyr Ser Val Gly Arg Asn Tyr Tyr Trp Gly
305                 310                 315                 320

Gly His Arg Val Thr Ser Tyr His Val Gly Gly Glu Asn Ile Arg Ser
                325                 330                 335

Pro Leu Tyr Gly Arg Glu Ala Asn Gln Glu Val Pro Arg Asp Phe Tyr
            340                 345                 350

Phe Tyr Gly Pro Val Phe Lys Thr Leu Ser Lys Pro Thr Leu Arg Pro
        355                 360                 365

Leu Gln Gln Pro Ala Pro Ala Pro Pro Phe Asn Leu Arg Ser Leu Glu
    370                 375                 380

Gly Val Glu Phe His Thr Pro Thr Gly Ser Phe Met Tyr Arg Glu Arg
385                 390                 395                 400

Gly Ser Val Asp Ser Phe Asn Glu Leu Pro Pro Phe Asn Pro Val Gly
                405                 410                 415

Leu Pro His Lys Val Tyr Ser His Arg Leu Cys His Ala Thr Phe Val
            420                 425                 430

Arg Lys Ser Gly Thr Pro Tyr Leu Thr Thr Gly Ala Ile Phe Ser Trp
        435                 440                 445
```

-continued

```
Thr His Arg Ser Ala Glu Glu Thr Asn Thr Ile Glu Ser Asn Ile Ile
    450                 455                 460

Thr Gln Ile Pro Leu Val Lys Ala Tyr Gln Ile Gly Ser Gly Thr Thr
465                 470                 475                 480

Val Arg Lys Gly Pro Gly Phe Thr Gly Gly Asp Ile Leu Arg Arg Thr
                485                 490                 495

Gly Pro Gly Thr Phe Gly Asp Met Arg Ile Asn Ile Asn Ala Pro Leu
            500                 505                 510

Ser Gln Arg Tyr Arg Val Arg Ile Arg Tyr Ala Ser Thr Thr Asp Leu
        515                 520                 525

Gln Phe Val Thr Ser Ile Asn Gly Thr Thr Ile Asn Ile Gly Asn Phe
    530                 535                 540

Pro Lys Thr Ile Asn Asn Leu Asn Thr Leu Gly Ser Glu Gly Tyr Arg
545                 550                 555                 560

Thr Val Ser Phe Ser Thr Pro Phe Ser Phe Ser Asn Ala Gln Ser Ile
                565                 570                 575

Phe Arg Leu Gly Ile Gln Ala Phe Ser Gly Val Gln Glu Val Tyr Val
            580                 585                 590

Asp Lys Ile Glu Phe Ile Pro Val Glu
        595                 600
```

AXMI-150 DELTA-ENDOTOXIN GENE AND METHODS FOR ITS USE

CROSS REFERENCE TO RELATED APPLICATION

This application claims the benefit of U.S. Provisional Application Ser. No. 61/140,427, filed Dec. 23, 2008, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "383057_SequenceListing.txt", created on Dec. 22, 2009, and having a size of 44 kilobytes and is filed concurrently with the specification. The sequence listing contained in this ASCII formatted document is part of the specification and is herein incorporated by reference in its entirety.

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

*Bacillus thuringiensis* is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiensis* strains or their insecticidal proteins can be used as environmentally-acceptable insecticides to control agricultural insect pests or insect vectors for a variety of human or animal diseases.

Crystal (Cry) proteins (delta-endotoxins) from *Bacillus thuringiensis* have potent insecticidal activity against predominantly Lepidopteran, Dipteran, and Coleopteran larvae. These proteins also have shown activity against *Hymenoptera, Homoptera*, Phthiraptera, Mallophaga, and Acari pest orders, as well as other invertebrate orders such as Nemathelminthes, Platyhelminthes, and Sarcomastigorphora (Feitelson (1993) The *Bacillus Thuringiensis* family tree. In *Advanced Engineered Pesticides*, Marcel Dekker, Inc., New York, N.Y.) These proteins were originally classified as CryI to CryV based primarily on their insecticidal activity. The major classes were *Lepidoptera*-specific (I), *Lepidoptera*-and Diptera-specific (II), Coleoptera-specific (III), Diptera-specific (IV), and nematode-specific (V) and (VI). The proteins were further classified into subfamilies; more highly related proteins within each family were assigned divisional letters such as Cry1A, Cry1B, Cry1C, etc. Even more closely related proteins within each division were given names such as Cry1C1, Cry1C2, etc.

A new nomenclature was recently described for the Cry genes based upon amino acid sequence homology rather than insect target specificity (Crickmore et al. (1998) *Microbiol. Mol. Biol. Rev.* 62:807-813). In the new classification, each toxin is assigned a unique name incorporating a primary rank (an Arabic number), a secondary rank (an uppercase letter), a tertiary rank (a lowercase letter), and a quaternary rank (another Arabic number). In the new classification, Roman numerals have been exchanged for Arabic numerals in the primary rank. Proteins with less than 45% sequence identity have different primary ranks, and the criteria for secondary and tertiary ranks are 78% and 95%, respectively.

The crystal protein does not exhibit insecticidal activity until it has been ingested and solubilized in the insect midgut. The ingested protoxin is hydrolyzed by proteases in the insect digestive tract to an active toxic molecule. (Höfte and Whiteley (1989) *Microbiol. Rev.* 53:242-255). This toxin binds to apical brush border receptors in the midgut of the target larvae and inserts into the apical membrane creating ion channels or pores, resulting in larval death.

Delta-endotoxins generally have five conserved sequence domains, and three conserved structural domains (see, for example, de Maagd et al. (2001)*Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Because of the devastation that insects can confer, and the improvement in yield by controlling insect pests, there is a continual need to discover new forms of pesticidal toxins.

SUMMARY OF INVENTION

Compositions and methods for conferring pesticidal activity to bacteria, plants, plant cells, tissues and seeds are provided. Compositions include nucleic acid molecules encoding sequences for pesticidal and insectidal polypeptides, vectors comprising those nucleic acid molecules, and host cells comprising the vectors. Compositions also include the pesticidal polypeptide sequences and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise transformed bacteria, plants, plant cells, tissues, and seeds.

In particular, isolated nucleic acid molecules are provided that encode a pesticidal protein. Additionally, amino acid sequences corresponding to the pesticidal protein are encompassed. In particular, the present invention provides for an isolated nucleic acid molecule comprising a nucleotide sequence encoding the amino acid sequence shown in SEQ ID NO:2 or a nucleotide sequence set forth in SEQ ID NO:1, 3, 4, 5, 6, 7, 8, 9, 10, 11, or 12, as well as variants and fragments thereof. Nucleotide sequences that are complementary to a nucleotide sequence of the invention, or that hybridize to a sequence of the invention are also encompassed.

Methods are provided for producing the polypeptides of the invention, and for using those polypeptides for controlling or killing a lepidopteran, coleopteran, nematode, or dipteran pest. Methods and kits for detecting the nucleic acids and polypeptides of the invention in a sample are also included.

The compositions and methods of the invention are useful for the production of organisms with enhanced pest resistance or tolerance. These organisms and compositions comprising the organisms are desirable for agricultural purposes. The compositions of the invention are also useful for generating altered or improved proteins that have pesticidal activity, or for detecting the presence of pesticidal proteins or nucleic acids in products or organisms.

The following embodiments are encompassed by the present invention:

1. An isolated nucleic acid molecule comprising a nucleotide sequence encoding an amino acid sequence having pesticidal activity, wherein said nucleotide sequence is selected from the group consisting of:
   a) the nucleotide sequence set forth in SEQ ID NO:1, 8, 9, 10, 11, or 12;
   b) a nucleotide sequence that encodes a polypeptide comprising the amino acid sequence of SEQ ID NO:2; and
   c) a nucleotide sequence that encodes a polypeptide comprising an amino acid sequence having at least 95% sequence identity to the amino acid sequence of SEQ ID NO:2.

2. The isolated nucleic acid molecule of embodiment 1, wherein said nucleotide sequence is a synthetic sequence that has been designed for expression in a plant.

3. The isolated nucleic acid molecule of embodiment 2, wherein said sequence is set forth in SEQ ID NO:3, 4, 5, 6, or 7.

4. A vector comprising the nucleic acid molecule of embodiment 1.

5. The vector of embodiment 4, further comprising a nucleic acid molecule encoding a heterologous polypeptide.

6. A host cell that contains the vector of embodiment 4.

7. The host cell of embodiment 6 that is a bacterial host cell.

8. The host cell of embodiment 6 that is a plant cell.

9. A transgenic plant comprising the host cell of embodiment 8.

10. The transgenic plant of embodiment 9, wherein said plant is selected from the group consisting of maize, sorghum, wheat, cabbage, sunflower, tomato, crucifers, peppers, potato, cotton, rice, soybean, sugarbeet, sugarcane, tobacco, barley, and oilseed rape.

11. A transgenic seed comprising the nucleic acid molecule of embodiment 1.

12. An isolated polypeptide with pesticidal activity, selected from the group consisting of:
   a) a polypeptide comprising the amino acid sequence of SEQ ID NO:2;
   b) a polypeptide comprising an amino acid sequence having at least 95% sequence identity to the amino acid sequence of SEQ ID NO:2; and
   c) a polypeptide that is encoded by SEQ ID NO:1.

13. The polypeptide of embodiment 12 further comprising heterologous amino acid sequences.

14. A composition comprising the polypeptide of embodiment 12.

15. The composition of embodiment 14, wherein said composition is selected from the group consisting of a powder, dust, pellet, granule, spray, emulsion, colloid, and solution.

16. The composition of embodiment 14, wherein said composition is prepared by desiccation, lyophilization, homogenization, extraction, filtration, centrifugation, sedimentation, or concentration of a culture of bacterial cells.

17. The composition of embodiment 14, comprising from about 1% to about 99% by weight of said polypeptide.

18. A method for controlling a lepidopteran, coleopteran, nematode, or dipteran pest population comprising contacting said population with a pesticidally-effective amount of a polypeptide of embodiment 12.

19. A method for killing a lepidopteran, coleopteran, nematode, or dipteran pest, comprising contacting said pest with, or feeding to said pest, a pesticidally-effective amount of a polypeptide of embodiment 12.

20. A method for producing a polypeptide with pesticidal activity, comprising culturing the host cell of embodiment 6 under conditions in which the nucleic acid molecule encoding the polypeptide is expressed.

21. A plant having stably incorporated into its genome a DNA construct comprising a nucleotide sequence that encodes a protein having pesticidal activity, wherein said nucleotide sequence is selected from the group consisting of:
   a) the nucleotide sequence set forth in SEQ ID NO:1, 8, 9, 10, 11, or 12;
   b) a nucleotide sequence that encodes a polypeptide comprising the amino acid sequence of SEQ ID NO:2; and
   c) a nucleotide sequence that encodes a polypeptide comprising an amino acid sequence having at least 95% sequence identity to the amino acid sequence of SEQ ID NO:2;

wherein said nucleotide sequence is operably linked to a promoter that drives expression of a coding sequence in a plant cell.

22. The plant of embodiment 21, wherein said plant is a plant cell.

23. A method for protecting a plant from a pest, comprising introducing into said plant or cell thereof at least one expression vector comprising a nucleotide sequence that encodes a pesticidal polypeptide, wherein said nucleotide sequence is selected from the group consisting of:
   a) the nucleotide sequence set forth in SEQ ID NO:1, 8, 9, 10, 11, or 12;
   b) a nucleotide sequence that encodes a polypeptide comprising the amino acid sequence of SEQ ID NO:2; and
   c) a nucleotide sequence that encodes a polypeptide comprising an amino acid sequence having at least 95% sequence identity to the amino acid sequence of SEQ ID NO:2.

24. The method of embodiment 23, wherein said plant produces a pesticidal polypeptide having pesticidal activity against a lepidopteran, coleopteran, nematode, or dipteran pest.

DETAILED DESCRIPTION

The present invention is drawn to compositions and methods for regulating pest resistance or tolerance in organisms, particularly plants or plant cells. By "resistance" is intended that the pest (e.g., insect) is killed upon ingestion or other contact with the polypeptides of the invention. By "tolerance" is intended an impairment or reduction in the movement, feeding, reproduction, or other functions of the pest. The methods involve transforming organisms with a nucleotide sequence encoding a pesticidal protein of the invention. In particular, the nucleotide sequences of the invention are useful for preparing plants and microorganisms that possess pesticidal activity. Thus, transformed bacteria, plants, plant cells, plant tissues and seeds are provided. Compositions are pesticidal nucleic acids and proteins of *Bacillus* or other species. The sequences find use in the construction of expression vectors for subsequent transformation into organisms of interest, as probes for the isolation of other homologous (or partially homologous) genes, and for the generation of altered pesticidal proteins by methods known in the art, such as domain swapping or DNA shuffling. The proteins find use in controlling or killing lepidopteran, coleopteran, dipteran, and nematode pest populations and for producing compositions with pesticidal activity.

By "pesticidal toxin" or "pesticidal protein" is intended a toxin that has toxic activity against one or more pests, including, but not limited to, members of the *Lepidoptera*, Diptera, and Coleoptera orders, or the Nematoda phylum, or a protein that has homology to such a protein. Pesticidal proteins have been isolated from organisms including, for example, *Bacillus* sp., *Clostridium bifermentans* and *Paenibacillus popilliae*. Pesticidal proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein.

Pesticidal proteins encompass delta-endotoxins. Delta-endotoxins include proteins identified as cry1 through cry43, cyt1 and cyt2, and Cyt-like toxin. There are currently over 250 known species of delta-endotoxins with a wide range of specificities and toxicities. For an expansive list see Crickmore et al. (1998), *Microbiol. Mol. Biol. Rev.* 62:807-813, and for regular updates see Crickmore et al. (2003) "*Bacillus thuringiensis* toxin nomenclature," at www.biols.susx.ac.uk/Home/Neil_Crickmore/Bt/index.

Thus, provided herein are novel isolated nucleotide sequences that confer pesticidal activity. These isolated nucleotide sequences encode polypeptides with homology to known delta-endotoxins or binary toxins. Also provided are the amino acid sequences of the pesticidal proteins. The protein resulting from translation of this gene allows cells to control or kill pests that ingest it.

Isolated Nucleic Acid Molecules, and Variants and Fragments Thereof

One aspect of the invention pertains to isolated or recombinant nucleic acid molecules comprising nucleotide sequences encoding pesticidal proteins and polypeptides or biologically active portions thereof, as well as nucleic acid molecules sufficient for use as hybridization probes to identify nucleic acid molecules encoding proteins with regions of sequence homology. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid sequence (or DNA) is used herein to refer to a nucleic acid sequence (or DNA) that is no longer in its natural environment, for example in an in vitro or in a recombinant bacterial or plant host cell. In some embodiments, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated delta-endotoxin encoding nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. In various embodiments, a delta-endotoxin protein that is substantially free of cellular material includes preparations of protein having less than about 30%, 20%, 10%, or 5% (by dry weight) of non-delta-endotoxin protein (also referred to herein as a "contaminating protein").

Nucleotide sequences encoding the proteins of the present invention include the sequence set forth in SEQ ID NO:1, 3, 4, 5, 6, 7, 8, 9, 10, 11, or 12, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the pesticidal protein encoded by this nucleotide sequence are set forth in SEQ ID NO:2, or the AXMI-004 amino acid sequences described in U.S. Pat. No. 7,355,089 and U.S. patent application Ser. No. 12/209,354, filed Sep. 12, 2008 entitled "Synthetic AXMI-004 Delta-endotoxin Genes and Methods for Their Use." both of which are incorporated by reference herein in their entirety.

Nucleic acid molecules that are fragments of these nucleotide sequences encoding pesticidal proteins are also encompassed by the present invention. By "fragment" is intended a portion of the nucleotide sequence encoding a pesticidal protein. A fragment of a nucleotide sequence may encode a biologically active portion of a pesticidal protein, or it may be a fragment that can be used as a hybridization probe or PCR primer using methods disclosed below. Nucleic acid molecules that are fragments of a nucleotide sequence encoding a pesticidal protein comprise at least about 50, 100, 200, 300, 400, 500, 600, 700, 800, 900, 1000, 1100, 1200, 1300, 1350, 1400 contiguous nucleotides, or up to the number of nucleotides present in a full-length nucleotide sequence encoding a pesticidal protein disclosed herein, depending upon the intended use. By "contiguous" nucleotides is intended nucleotide residues that are immediately adjacent to one another. Fragments of the nucleotide sequences of the present invention will encode protein fragments that retain the biological activity of the pesticidal protein and, hence, retain pesticidal activity. By "retains activity" is intended that the fragment will have at least about 30%, at least about 50%, at least about 70%, 80%, 90%, 95% or higher of the pesticidal activity of the pesticidal protein. In one embodiment, the pesticidal activity is coleoptericidal activity. In another embodiment, the pesticidal activity is lepidoptericidal activity. In another embodiment, the pesticidal activity is nematocidal activity. In another embodiment, the pesticidal activity is diptericidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a nucleotide sequence encoding a pesticidal protein that encodes a biologically active portion of a protein of the invention will encode at least about 15, 25, 30, 50, 75, 100, 125, 150, 175, 200, 250, 300, 350, 400, 450 contiguous amino acids, or up to the total number of amino acids present in a full-length pesticidal protein of the invention.

Preferred pesticidal proteins of the present invention are encoded by a nucleotide sequence sufficiently identical to the nucleotide sequence of SEQ ID NO:1, 3, 4, 5, 6, 7, 8, 9, 10, 11, or 12. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the percent identity is calculated across the entirety of the reference sequence (i.e., the sequence disclosed herein as any of SEQ ID NO:1, 3, 4, 5, 6, 7, 8, 9, 10, 11, or 12). The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to pesticidal-like nucleic acid molecules of the invention. BLAST protein searches can be performed with the BLASTX program, score=50, wordlength=3, to obtain amino acid sequences homologous to pesticidal protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules. "Variants" of the pesticidal protein encoding nucleotide sequences include those sequences that encode the pesticidal proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the pesticidal proteins disclosed in the present invention as discussed below. Variant proteins encompassed by the present invention are biologically active, that is they continue to possess the desired biological activity of the native protein, that is, pesticidal activity. By "retains activity" is intended that the variant will have at least about 30%, at least about 50%, at least about 70%, or at least about 80% of the pesticidal activity of the native protein. Methods for measuring pesticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

The skilled artisan will further appreciate that changes can be introduced by mutation of the nucleotide sequences of the invention thereby leading to changes in the amino acid sequence of the encoded pesticidal proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more, predicted, nonessential amino acid residues. A "nonessential" amino acid residue is a residue that can be altered from the wild-type sequence of a pesticidal protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the invention (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the invention (e.g., residues that have only conservative substitutions between all proteins contained in the alignment homologous proteins). However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

Using methods such as PCR, hybridization, and the like corresponding pesticidal sequences can be identified, such sequences having substantial identity to the sequences of the invention. See, for example, Sambrook and Russell (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the pesticidal nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known pesticidal protein-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, or 200 consecutive nucleotides of nucleotide sequence encoding a pesticidal protein of the invention or a fragment or variant thereof. Methods for the preparation of probes for hybridization are generally known in the art and are disclosed in Sambrook and Russell, 2001, supra herein incorporated by reference.

For example, an entire pesticidal protein sequence disclosed herein, or one or more portions thereof, may be used as a probe capable of specifically hybridizing to corresponding pesticidal protein-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Pesticidal proteins are also encompassed within the present invention. By "pesticidal protein" is intended a protein having the amino acid sequence set forth in SEQ ID NO:2. Fragments, biologically active portions, and variants thereof are also provided, and may be used to practice the methods of the present invention. An "isolated protein" is used to refer to a protein that is no longer in its natural environment, for example in vitro or in a recombinant bacterial or plant host cell.

"Fragments" or "biologically active portions" include polypeptide fragments comprising amino acid sequences sufficiently identical to the amino acid sequence set forth in SEQ ID NO:2, and that exhibit pesticidal activity. A biologically active portion of a pesticidal protein can be a polypeptide that is, for example, 10, 25, 50, 100, 150, 200, 250 or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of SEQ ID NO:2. The invention encompasses other fragments, however, such as any fragment in the protein greater than about 10, 20, 30, 50, 100, 150, 200, 250, or 300 amino acids.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of SEQ ID NO:2. Variants also include polypeptides encoded by a nucleic acid molecule that hybridizes to the nucleic acid molecule of SEQ ID NO:1, 3, 4, 5, 6, 7, 8, 9, 10, 11, or 12, or a complement thereof, under stringent conditions. Variants include polypeptides that differ in amino acid sequence due to mutagenesis. See, for example, the variants disclosed in the Experimental Examples section herein. Variant proteins encompassed by the present invention are biologically active, that is they continue to possess the desired biological activity of the native protein, that is, retaining pesticidal activity. In some embodiments, the variants have improved activity relative to the native protein. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

Bacterial genes, such as the axmi genes of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present invention and may be used in the methods of the present invention. It will be understood that, when expressed in plants, it will be necessary to alter the alternate start codon to ATG for proper translation.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Altered or Improved Variants

It is recognized that DNA sequences of a pesticidal protein may be altered by various methods, and that these alterations may result in DNA sequences encoding proteins with amino acid sequences different than that encoded by a pesticidal protein of the present invention. This protein may be altered in various ways including amino acid substitutions, deletions, truncations, and insertions of one or more amino acids of SEQ ID NO:2, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions or insertions. Methods for such manipulations are generally known in the art. For example, amino acid sequence variants of a pesticidal protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a pesticidal protein to confer pesticidal activity may be improved by the use of such techniques upon the compositions of this invention. For example, one may express a pesticidal protein in host cells that exhibit high rates of base misincorporation during DNA replication, such as XL-1 Red (Stratagene, La Jolla, Calif.). After propagation in such strains, one can isolate the DNA (for example by preparing plasmid DNA, or by amplifying by PCR and cloning the resulting PCR fragment into a vector), culture the pesticidal protein mutations in a non-mutagenic strain, and identify mutated genes with pesticidal activity, for example by performing an assay to test for pesticidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different pesticidal protein coding regions can be used to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene of the invention and other known pesticidal genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered pesticidal proteins. Domains may be swapped between pesticidal proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem.* 265:20923-20930; Rang et al. 91999) *Appl. Environ. Microbiol.* 65:2918-2925).

Vectors

A pesticidal sequence of the invention may be provided in an expression cassette for expression in a plant of interest. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are protolytically activated in the gut of the target pest (Chang (1987) *Methods Enzymol.* 153:507-516). In some embodiments of the present invention, the signal sequence is located in the native sequence, or may be derived from a sequence of the invention. By "leader sequence" is intended any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the pesticidal sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

In one embodiment, the pesticidal protein is targeted to the chloroplast for expression. In this manner, where the pesticidal protein is not directly inserted into the chloroplast, the expression cassette will additionally contain a nucleic acid encoding a transit peptide to direct the pesticidal protein to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The pesticidal gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell.

"Heterologous" generally refers to the nucleic acid sequences that are not endogenous to the cell or part of the native genome in which they are present, and have been added to the cell by infection, transfection, microinjection, electroporation, microprojection, or the like.

Transformation of plant cells can be accomplished by one of several techniques known in the art. The pesticidal gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}P$ target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the pesticidal gene is then tested by hybridizing the filter to a radioactive probe derived from a pesticidal gene, by methods known in the art (Sambrook and Russell, 2001, supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the pesticidal protein.

Pesticidal Activity in Plants

In another aspect of the invention, one may generate transgenic plants expressing a pesticidal protein that has pesticidal activity. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a pesticidal protein may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pesticidal activity.

Fertile plants expressing a pesticidal protein may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassaya, coffee, coconut, pineapple, citrus trees, cocoa, tea, banana, avocado, fig, guava, mango, olive, papaya, cashew, *macadamia*, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape., etc.).

Use in Pesticidal Control

General methods for employing strains comprising a nucleotide sequence of the present invention, or a variant thereof, in pesticide control or in engineering other organisms as pesticidal agents are known in the art. See, for example U.S. Pat. No. 5,039,523 and EP 0480762A2.

The *Bacillus* strains containing a nucleotide sequence of the present invention, or a variant thereof, or the microorganisms that have been genetically altered to contain a pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a pesticidal gene into a cellular host. Expression of the pesticidal gene results, directly or indirectly, in the intracellular production and maintenance of the pesticide. In one aspect of this invention, these cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing a gene of this invention such as to allow application of the resulting material as a pesticide.

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible “baits” or fashioned into pest “traps” to permit feeding or ingestion by a target pest of the pesticidal formulation.

Methods of applying an active ingredient of the present invention or an agrochemical composition of the present invention that contains at least one of the pesticidal proteins produced by the bacterial strains of the present invention include leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran, dipteran, or coleopteran pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

"Pest" includes but is not limited to, insects, fungi, bacteria, nematodes, mites, ticks, and the like. Insect pests include insects selected from the orders Coleoptera, Diptera, *Hymenoptera, Lepidoptera*, Mallophaga, *Homoptera*, Hemiptera, Orthroptera, Thysanoptera, *Dermaptera, Isoptera*, Anoplura, *Siphonaptera*, Trichoptera, etc., particularly Coleoptera, *Lepidoptera*, and Diptera.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrimidae. Superfamily Hydrophiloidea includes the family Hydrophilidae. Superfamily Staphylinoidea includes the families Silphidae and Staphylimidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachinidae, Anthomyiidae, Muscidae, Calliphoridae, and Sarcophagidae.

The order *Lepidoptera* includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, and Tineidae.

Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus* leucopterus, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus* leucopterus, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punc-*

*tata*, clover leaf weevil; *Diabrotica undecimpunctata* howardi, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctate*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Methods for Increasing Plant Yield

Methods for increasing plant yield are provided. The methods comprise introducing into a plant or plant cell a polynucleotide comprising a pesticidal sequence disclosed herein. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

The plants can also be treated with one or more chemical compositions, including one or more herbicide, insecticides, or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halosulfuron Gowan, Paraquat, Propyzamide, Sethoxydim, Butafenacil, Halosulfuron, Indaziflam; Fruits/Vegetables Insecticides: Aldicarb, *Bacillus thuriengiensis*, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, Fluacrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, Indoxacarb, Forthiazate, Fenamiphos, Cadusaphos, Pyriproxifen, Fenbutatin-oxid, Hexthiazox, Methomyl, 4-[[(6-Chlorpyridin-3-yl)methyl](2,2-difluorethyl)amino]furan-2(5H)-on; Fruits/Vegetables Fungicides: Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, Ioxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethon-methyl, Pirimicarb, Methiocarb; Maize Herbicides: Atrazine, Alachlor, Bromoxynil, Acetochlor, Dicamba, Clopyralid, (S-)Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides:

Carbofuran, Organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

The following examples are offered by way of illustration and not by way of limitation.

EXPERIMENTAL EXAMPLES

Example 1

Extraction of Plasmid DNA

The complete gene sequence was identified from the selected strain via the MiDAS genomics approach as follows:

Preparation of Extrachromosomal DNA from the Strain. Extrachromosomal DNA contains a mixture of some or all of the following: plasmids of various size; phage chromosomes; genomic DNA fragments not separated by the purification protocol; other uncharacterized extrachromosomal molecules.

Mechanical or enzymatic shearing of the extrachromosomal DNA to generate size-distributed fragments.

Sequencing of the fragmented DNA by high-throughput pyrosequencing methods.

Identification of putative toxin genes via homology and/or other computational analyses.

When required, sequence finishing of the gene of interest by one of several PCR or cloning strategies (e.g. TAIL-PCR).

Example 2

Heterologous expression of AXMI-150

The complete ORF of axmi-150 (~2 kb which encode ~77.5 kD protein) was cloned into an *E. coli* expression vector based on pRSF1b (to give pAX5482). Gene sequence of axmi-150 starting with an internal methionine (19 amino acids downstream from the original methionine in pAX5482) was also cloned in the pRSF1b based vector to give pAX5484.

The sequence encoding axmi-150 was also cloned in a *Bacillus* expression vector based on pAX916 (to give pAX5483). All of the resulting clones were confirmed by restriction analysis and finally, by complete sequencing of the cloned gene.

For expression in *E. coli*, BL21*DE3 was transformed with pAX5482 or pAX5484. Single colony was inoculated in LB supplemented with kanamycin and grown overnight at 37° C. The following day, fresh medium was inoculated in duplicate with 1% of overnight culture and grown at 37° C. to logarithmic phase. Subsequently, cultures were induced with 1 mM IPTG for 3 hours at 37° C. or overnight at 20° C. Each cell pellet was suspended in 50 mM sodium carbonate buffer, pH 10.5 supplemented with 1 mM DTT and sonicated. Analysis by SDS-PAGE detected expression of a ~78 kD protein corresponding to AXMI-150.

For expression in *Bacillus*, Bt51 was transformed with pAX5483 and a single colony was grown in CYS-glu medium for 3 days to sporulation. Cell pellet was then extracted with 50 mM Tris Cl buffer, pH 8.0 or 50 mM sodium carbonate buffer, pH 10.5, each supplemented with 1 mM DTT. Soluble fraction showed presence of a 78 kD Axmil50 protein. Trypsinization of AXMI-150 gave a faint protein band of about 55 kD. The sequence of the axmi-150 open reading frame is provided herein as SEQ ID NO:1 and encodes the AXMI-150 protein (SEQ ID NO:2).

Searching of the AXMI-150 amino acid sequence versus public sequence databases shows that AXMI-150 is homologous to the AXMI-004 protein (U.S. Pat. No. 7,355,099). AXMI-150 also exhibits amino acid homology to cry1Ca4, and to a group of AXMI-004-like proteins described in International Application Publication No. WO2005/107383.

Known homologs and approximate percent identity:
AXMI-004-85.5%
Cry1Ca4 (toxin domain)-51.8%

Example 3

Pesticidal Activity of AXMI-150

Soluble extracts containing AXMI-150 were tested in insect assays with appropriate controls. A 5 day read of the plates showed AXMI-150 to have pesticidal activity on European Corn Borer (ECB), velvetbean caterpillar (VBC), and high mortality (>50%) on diamondback moth (DBM) and Southwest corn borer (SWCB). Table 1 shows a description of the scoring assignments used herein.

TABLE 1

Description of Scoring System

| Score | Description |
|---|---|
| 0 | no effect observed |
| 1 | mild non-uniform stunting |
| 2 | moderate non-uniform stunting |
| 3 | moderate to severe uniform stunting |
| 4 | mortality (<100%) with uniform stunting |
| 5 | complete mortality |

TABLE 2

Pesticidal Activity of AXMI-150.

| Pest | Activity of AXMI-150 |
|---|---|
| European Corn Borer | +++ |
| Velvet Bean Caterpillar | + |
| Diamondback Moth | +++++ |
| Southwest Corn borer | ++++ |

Example 4

Additional Assays for Pesticidal Activity

The nucleotide sequences of the invention can be tested for their ability to produce pesticidal proteins. The ability of a pesticidal protein to act as a pesticide upon a pest is often assessed in a number of ways. One way well known in the art is to perform a feeding assay. In such a feeding assay, one exposes the pest to a sample containing either compounds to be tested or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson and Preisler, eds. (1992) *Pesticide bioassays with arthropods*, CRC, Boca Raton, Fla. Alternatively, assays are commonly described in the journals *Arthropod Management Tests* and *Journal of Economic Entomology* or by discussion with members of the Entomological Society of America (ESA).

Example 5

Directed Evolution of AXMI-004

Directed evolution was performed on AXMI-004 (SEQ ID NO:14). Three loops in the receptor binding region were targeted for mutagenesis. As a first step, deletions of loops 1 (corresponding to residues 311-316 of SEQ ID NO:14), 2 (corresponding to residues 368-378 of SEQ ID NO:14) and 3 (corresponding to residues 434-438 of SEQ ID NO:14) were generated, expressed in Bt51 and tested for bioactivity. Deletions of loops 2 and 3 severely decreased protein solubility, whereas deletion of loop 1 did not affect protein solubility. The loop 1 deletion variant showed reduced toxicity against European corn borer (ECB), but retained its activity against Diamondback moth (DBM). Next, within these 3 loops, a total of 23 positions were mutagenized. A set of point mutants was generated.

Plasmid pAX5485 (His6-axmi004-m2 in pRSF1b) was used for expression of wt axmi-004 and was also the basis for mutagenesis and variant expression.

Mutagenesis was carried out using the QUIKCHANGE® lightning site directed mutagenesis kit (Stratagene), mutants were sequenced, and unique variants were identified. The following point mutant diversity was generated:

TABLE 3

| Loop 1: | | | | | | |
|---|---|---|---|---|---|---|
| | Position | | | | | |
| | 311 | 312 | 313 | 314 | 315 | 316 |
| Wt | Y | S | V | G | R | N |
| Diversity | G | R | G | P | G | G |
| | C | G | R | R | A | R |
| | R | P | T | C | C | A |
| | S | C | A | S | S | S |
| | T | A | I | A | T | P |
| | A | E | H | T | W | T |
| | P | Q | D | W | P | W |
| | V | H | Q | H | N | K |
| | E | V | L | L | E | I |
| | L | N | E | V | L | E |
| | K | L | M | D | V | F |
| | Q | D | | M | K | V |
| | D | K | | E | Y | Q |
| | I | | | K | D | |
| | | | | | Q | |
| | | | | | I | |
| TOTAL | 14 | 13 | 11 | 14 | 16 | 13 |

TABLE 4

| Loop2: | | | | | | | | | | | |
|---|---|---|---|---|---|---|---|---|---|---|---|
| | Position | | | | | | | | | | |
| | 368 | 369 | 370 | 371 | 372 | 373 | 374 | 375 | 376 | 377 | 378 |
| wt | P | L | Q | Q | P | A | P | A | P | P | F |
| | A | A | P | R | D | G | R | G | S | C | A |
| | G | W | S | P | K | R | G | W | G | S | C |
| | T | G | G | S | V | S | A | C | T | T | T |
| | S | T | R | G | L | C | S | S | W | A | W |
| | C | R | W | T | N | P | T | R | C | W | G |
| | R | M | A | L | E | T | W | D | A | R | S |
| | L | F | T | V | F | V | V | L | R | G | R |
| | Q | K | V | H | H | N | H | V | I | I | V |
| | V | E | E | K | Q | E | F | K | V | L | Y |
| | N | V | L | F | M | D | L | I | L | H | K |
| | D | H | Y | N | A | M | D | E | D | V | Q |
| | E | I | I | D | G | I | Y | H | E | K | E |
| | H | | | Y | R | F | Q | Q | Q | Q | I |
| | I | | | M | T | K | E | M | M | D | L |
| | | | | E | S | E | M | | N | E | I |
| | | | | | W | L | N | | H | Y | D |
| | | | | | | Y | | | | | |
| | | | | | | H | | | | | |
| TOTAL | 14 | 12 | 12 | 15 | 16 | 18 | 14 | 14 | 16 | 16 | 16 |

TABLE 5

| Loop 3: | | | | | |
|---|---|---|---|---|---|
| | Position | | | | |
| | 434 | 435 | 436 | 437 | 438 |
| wt | K | S | G | T | P |
| MUTANTS | T | R | P | A | G |
| | G | T | R | G | R |
| | A | G | T | P | T |
| | R | A | A | T | S |
| | S | P | S | S | W |
| | W | W | V | R | A |
| | P | L | K | I | F |
| | E | E | E | M | L |
| | Q | V | L | E | V |
| | V | M | D | H | Q |
| | L | D | H | Y | K |
| | N | H | Q | V | F |
| | F | | N | K | I |
| | M | | | D | P |
| | I | | | F | N |
| | K | | | L | |
| | H | | | N | |
| TOTAL | 17 | 12 | 13 | 17 | 15 |

Variants for loop 1, loop 2 and loop 3 were pooled separately.

Library Expression and Screening:

Primary Screening:

The pooled library variants, as well as pAX5485 were transformed into BL21*DE3 cells and plated on LB+Kanamycin (100 μm/ml). Fresh colonies were picked into 16 ml LB+Kanamycin (100 μm/ml) liquid medium and were grown in 24 deep well blocks at 37 degrees C. and 300 rpm until an OD600 nm of 0.3-0.4 was reached. IPTG was added to a final concentration of 0.5 mM and the cultures were incubated for an additional 18 hours at 20 degrees C. The OD600 nm was determined and the cells were collected by centrifugation (10 minutes at 4500 rpm, 4 degrees C.). The cell pellets were resuspended in 50 mM Sodium carbonate pH 10.5, 1 mM DTT at a density of 10 OD600/ml. The cells were disrupted by bead beating and soluble extracts were obtained after centrifugation at 4000 rpm for 15 minutes at 4 degrees C.

The extracts were assayed for activity against ECB, Southwestern corn borer (SWCB), *Heliothis virescens* (Hz), Velvetbean caterpillar (VBC) and DBM at 4 replicates per variant each. After 5 days, toxicity scores were determined by averaging the scores from 4 replicates. 122 variants of the loop 1 pool, 240 variants of the loop 2 pool, and 121 variants of the loop 3 pool, respectively, were assayed in this primary screen, providing a 1.5× coverage of the library.

Re-Assays and Scale-Up:

Variants showing improved scores on ECB or SWCB were sequenced and re-assayed at 4 replicates per variant. Variants that showed again improved activity against ECB or SWCB were selected for scale-up.

For scale-ups, 3 freshly transformed colonies were picked into 70 ml LB+Kanamycin (100 μg/ml) and grown in 0.5 liter shaker flasks at 37 degrees C. and 150 rpm until an OD600 nm of 0.3-0.4 was reached. IPTG was added to a final concentration of 0.5 mM and the cultures were incubated for an additional 18 hours at 20 degrees C. The OD600 nm was determined and the cells were collected by centrifugation (10 minutes at 5000 rpm, 4 degrees C.). The cell pellets were resuspended in 50 mM sodium carbonate pH10.5, 1 mM DTT at a density of 100D600/ml. The cells were disrupted by bead beating and soluble extracts were obtained after centrifugation at 4000 rpm for 15 minutes at 4 degrees C. Axmi-004 variants in those extracts were quantitated on SDS-PAGE stained with Coomassie by comparing serial dilutions of extract to a BSA standard of known concentration. All variant protein tested express at very similar levels. Scaled-up preps were assayed against ECB, SWCB, VBC, Hz, and DBM at 16 replicates per variant and pest. Scores were averaged.

The following loop2 variants showed improved toxicity in the primary screen, re-assay and in scale-ups:

TABLE 6

| | ECB | | SWCB | |
|---|---|---|---|---|
| | Stunting | Percent Mortality | Stunting | Percent Mortality |
| axmi-004 | +++ | 13% | − | 6% |
| L21B11 | + | 9% | + | 16% |
| L21F2 | ++ | 6% | + | 14% |
| L23G5 | + | 9% | + | 16% |
| L21A5 | ++ | | − | — |
| L22H7 | ++ | | | |
| L22E7 | + | | | |
| L22F7 | ++ | | | |
| pRSF1b | − | — | | |

The sequence diversity at positions 370, 373, 376, and 377 is shown in Table 7:

TABLE 7

| | 370 | 371 | 372 | 373 | 374 | 375 | 376 | 377 | 378 |
|---|---|---|---|---|---|---|---|---|---|
| AXMI004 | Q | Q | P | A | P | A | P | P | F |
| L21A5 | Q | Q | P | A | P | A | P | Q | F |
| L21F2 | R | Q | P | A | P | A | P | P | F |
| L21B11 | Q | Q | P | A | P | A | T | P | F |
| L22F7 | Q | Q | P | A | P | A | G | P | F |
| L23G5 | Q | Q | P | M | P | A | P | P | F |

Three variants from the loop1 library showed improved toxicity in the primary assay and the re-assay (Table 8).

TABLE 8

| | Hz | ECB | VBC | DBM | SWCB |
|---|---|---|---|---|---|
| axmi004 | − | + | ++ | +++++ | + |
| LL1H11 | − | ++ | + | +++++ | + |
| L11E8 | − | ++ | ++ | +++++ | no data |
| L11F9 | + | ++ | + | +++++ | no data |

All three of the improved variants are mutated at position 316 of SEQ ID NO:14, where the asparagine residue was mutated to valine, proline, or phenylalanine in mutants L11E8, L11F9, and L11H11, respectively, suggesting that an important position linked to improved activity has been identified.

The following loop 3 variants showed improved toxicity in the primary screen, re-assay of ECB activity and in scale-ups:

TABLE 9

| | Stunt score | Mortality (percent) |
|---|---|---|
| AXMI004 | ++ | 28% |
| L31B10 | ++ | no data |
| L31A11 | ++ | 20% |
| L31H11 | ++ | 33% |

The improved variants are mutated from lysine at position 434 of AXMI004 to threonine and valine in mutants L31B10 and L31A11, respectively, and from proline at position 438 of AXMI004 to serine in mutant L31H11. In a simulated crystal structure of these AXMI004, the side chains of mutated positions in loops 1, 2, and 3 all face in the same general direction. This finding suggests that amino acids in several loops may contribute to a common binding interface. Additional permutations incorporating functionally improved diversity in several loops may thus provide even further improvements in activity.

Example 6

Directed Evolution of AXMI-150

This example describes the directed evolution of AXMI-150 (SEQ ID NO:2). A loop in the putative processing region has been targeted for mutagenesis.

Plasmid pAX5482 (His6-axmil50 in pRSF1b) was used for expression of wt axmi-150 and was also the basis for mutagenesis and variant expression. Mutagenesis was carried out using the QUIKCHANGE® lightning kit (Stratagene), mutants were sequenced and unique variants were identified. The following point mutant diversity was generated:

TABLE 10

| | 116 | 117 | 118 | 119 | 120 | 121 | 122 |
|---|---|---|---|---|---|---|---|
| AXMI150 | N | N | T | G | S | S | K |
| | P | T | S | A | P | A | G |
| | R | G | P | S | T | G | C |
| | T | S | A | E | R | T | P |
| | G | C | R | M | C | P | S |
| | Y | A | G | V | A | R | T |
| | Q | P | N | L | G | Q | R |
| | K | R | D | Q | L | E | H |
| | A | K | M | D | E | L | I |
| | W | E | L | H | Q | H | E |
| | S | M | V | K | H | D | N |

TABLE 10-continued

| | 116 | 117 | 118 | 119 | 120 | 121 | 122 |
|---|---|---|---|---|---|---|---|
| | | F | H | | V | V | D |
| | | | E | | | F | L |
| | | | Y | | | | Y |
| | | | K | | | | M |
| | | | | | | | Q |
| TOTAL | 10 | 11 | 14 | 10 | 11 | 12 | 15 |

Library Expression and Screening:

Primary Screening:

The pooled library variants, as well as the pAX5482 were transformed into BL21*DE3 cells and plated on LB+Kanamycin (100 ug/ml). Fresh colonies were picked into 16 ml LB+Kanamycin (100 ug/ml) liquid medium and were grown in 24 deep well blocks at 37 degrees C. and 300 rpm until an OD600 nm of 0.3-0.4 was reached. IPTG was added to a final concentration of 0.5 mM and the cultures were incubated for an additional 18 hours at 20 degrees C. The OD600 nm was determined and the cells were collected by centrifugation (10 minutes at 4500 rpm, 4 degrees C.). The cell pellets were resuspended in 50 mM Sodium carbonate pH10.5, 1 mM DTT at a density of 10 OD600/ml. The cells were disrupted by bead beating and soluble extracts were obtained after centrifugation at 4000 rpm for 15 minutes at 4 degrees C.

The extracts were assayed for activity against ECB, SWCB, Hz, VBC and DBM at 4 replicates per variant each. After 5 days, toxicity scores were determined by averaging the scores from 4 replicates. 119 variants were screened, giving 1.5× coverage of the library.

Re-Assays and Scale-Up:

Variants showing improved scores on ECB or SWCB were sequenced and re-assayed at 4 replicates per variant. Variants that showed again improved activity against ECB or SWCB were selected for scale-up.

For scale-ups, 3 freshly transformed colonies were picked into 70 ml LB+Kanamycin (100 μg/ml) and grown in 0.5 liter shaker flasks at 37 degrees C. and 150 rpm until an OD600 nm of 0.3-0.4 was reached. IPTG was added to a final concentration of 0.5 mM and the cultures were incubated for an additional 18 hours at 20 degrees C. The OD600 nm was determined and the cells were collected by centrifugation (10 minutes at 5000 rpm, 4 degrees C.). The cell pellets were resuspended in 50 mM sodium carbonate pH10.5, 1 mM DTT at a density of 100D600/ml. The cells were disrupted by bead beating and soluble extracts were obtained after centrifugation at 4000 rpm for 15 minutes at 4 degrees C. Axmi-150 variants in those extracts were quantitated on SDS-PAGE stained with Coomassie by comparing serial dilutions of extract to a BSA standard of known concentration. All variant protein tested express at very similar levels. Scaled-up preps were assayed against ECB, SWCB, VBC, Hz, and DBM at 16 replicates per variant and pest. Scores were averaged and standard deviations were determined. The activities of variants showing improvements in scale-ups are shown in Tables 11-13 below:

TABLE 11

| | ECB activity | | SWCB activity | |
|---|---|---|---|---|
| n = 16 | Stunt score | Mortality | Stunt score | Mortality |
| AXMI150 | + | – | +++ | 25% |
| L11D3 | + | – | +++ | 38% |
| L11D6 | – | – | +++ | 25% |
| L11B6 | + | – | +++ | 16% |
| L11E5 | – | – | +++ | 19% |
| pRSF1b | – | – | – | — |

TABLE 12

| | ECB activity | | SWCB activity | |
|---|---|---|---|---|
| n = 16 | Stunt score | Mortality | Stunt score | Mortality |
| AXMI150 | + | 8% | +++ (n = 12) | 58% |
| L11C10 | + | 13% | ++++ | 97% |
| L11D10 | ++ | 8% | +++ | 75% |
| L11F10 | + | — | +++ | 72% |
| L11E12 | + | — | + (n = 12) | 31% |

TABLE 13

| | ECB activity | | SWCB activity | |
|---|---|---|---|---|
| n = 16 | Stunt score | Mortality | Stunt score | Mortality |
| AXMI150 | + | — | +++ | 41% |
| L11G5 | – | — | – | 6% |
| L11D1 | – | 2% | +++ | 64% |
| L11A6 | – | 3% | ++ | 41% |
| L11B5 | – | 5% | + | 19% |
| L12C1 | – | — | ++ | 37% |

The sequence diversity in those improved variants is described below:

TABLE 14

| | 116 | 117 | 118 | 119 | 120 | 121 | 122 |
|---|---|---|---|---|---|---|---|
| AXMI150 | N | N | T | G | S | S | K |
| L11A6 | N | N | S | G | S | S | K |
| L11B5 | N | N | N | G | S | A | K |
| L11B6 | N | N | T | G | S | S | K |
| L11C10 | K | N | T | G | S | S | K |
| L11D1 | N | N | T | G | G | S | K |
| L11D10 | N | N | T | G | Q | S | K |
| L11D3 | N | N | T | K | S | S | K |
| L11F10 | N | N | T | G | S | P | K |

Example 7

Vectoring of Genes for Plant Expression

The coding regions of the invention are connected with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter—gene—terminator constructs also are well known in the art.

In one aspect of the invention, synthetic DNA sequences are designed and generated. These synthetic sequences have altered nucleotide sequence relative to the parent sequence, but encode proteins that are essentially identical to the parent AXMI-150 protein (e.g., SEQ ID NO:3, 4, 5, 6, or 7).

In another aspect of the invention, synthetic DNA sequences encoding proteins that are essentially identical to the AXMI-004 protein (e.g., SEQ ID NO:8-12) are encompassed. The AXMI-004 protein is described in U.S. Pat. No. 7,355,089 and U.S. patent application Ser. No. 12/209,354, filed Sep. 12, 2008 entitled "Synthetic AXMI-004 Delta-endotoxin Genes and Methods for Their Use."

In another aspect of the invention, modified versions of the synthetic genes are designed such that the resulting peptide is targeted to a plant organelle, such as the endoplasmic reticulum or the apoplast. Peptide sequences known to result in targeting of fusion proteins to plant organelles are known in the art. For example, the N-terminal region of the acid phosphatase gene from the White Lupin *Lupinus albus* (GENBANK® ID GI:14276838, Miller et al. (2001) *Plant Physiology* 127: 594-606) is known in the art to result in endoplasmic reticulum targeting of heterologous proteins. If the resulting fusion protein also contains an endoplasmic reticulum retention sequence comprising the peptide N-terminus-lysine-aspartic acid-glutamic acid-leucine (i.e., the "KDEL" motif, SEQ ID NO:13) at the C-terminus, the fusion protein will be targeted to the endoplasmic reticulum. If the fusion protein lacks an endoplasmic reticulum targeting sequence at the C-terminus, the protein will be targeted to the endoplasmic reticulum, but will ultimately be sequestered in the apoplast.

Thus, this gene encodes a fusion protein that contains the N-terminal thirty-one amino acids of the acid phosphatase gene from the White Lupin *Lupinus albus* (GENBANK® ID GI:14276838, Miller et al., 2001, supra) fused to the N-terminus of the amino acid sequence of the invention, as well as the KDEL sequence at the C-terminus. Thus, the resulting protein is predicted to be targeted the plant endoplasmic reticulum upon expression in a plant cell.

The plant expression cassettes described above are combined with an appropriate plant selectable marker to aid in the selection of transformed cells and tissues, and ligated into plant transformation vectors. These may include binary vectors from *Agrobacterium*-mediated transformation or simple plasmid vectors for aerosol or biolistic transformation.

Example 8

Vectoring genes for Plant Expression

The coding region DNA of the genes of the invention are operably connected with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter—gene—terminator constructs also are well known in the art.

The plant expression cassettes described above are combined with an appropriate plant selectable marker to aid in the selections of transformed cells and tissues, and ligated into plant transformation vectors. These may include binary vectors from *Agrobacterium*-mediated transformation or simple plasmid vectors for aerosol or biolistic transformation.

Example 9

Transformation of Maize Cells with the Pesticidal Protein Genes Described Herein Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to the genes of the invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

DN62A5S Media

| Components | Per Liter | Source |
|---|---|---|
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

The pH of the solution is adjusted to pH 5.8 with 1N KOH/1N KCl, Gelrite (Sigma) is added at a concentration up to 3 g/L, and the media is autoclaved. After cooling to 50° C., 2 ml/L of a 5 mg/ml stock solution of silver nitrate (Phytotechnology Labs) is added.

Example 10

Transformation of Genes of the Invention in Plant Cells by *Agrobacterium*-Mediated Transformation Ears are best collected 8-12 days after pollination. Embryos are isolated from the ears, and those embryos 0.8-

1.5 mm in size are preferred for use in transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

---

That which is claimed:

1. An isolated polypeptide with pesticidal activity, wherein said polypeptide comprises an amino acid sequence having at least 95% sequence identity to the amino acid sequence of SEQ ID NO:2, and wherein said polypeptide comprises the following amino acid substitution relative to SEQ ID NO:2:

a) a lysine at the position corresponding to amino acid residue 116 of SEQ ID NO:2;

b) a glutamine at the position corresponding to amino acid residue 120 of SEQ ID NO:2: or c) a proline at the position corresponding to amino acid residue 121 of SEQ ID NO:2.

2. The polypeptide of claim 1 further comprising heterologous amino acid sequences.

3. A composition comprising the polypeptide of claim 1.

4. The composition of claim 3, wherein said composition is selected from the group consisting of a powder, dust, pellet, granule, spray, emulsion, colloid, and solution.

5. The composition of claim 4, wherein said composition is prepared by desiccation, lyophilization, homogenization, extraction, filtration, centrifugation, sedimentation, or concentration of a culture of bacterial cells.

6. The composition of claim 4, comprising from about 1% to about 99% by weight of said polypeptide.

7. A method for controlling a lepidopteran, coleopteran, nematode, or dipteran pest population comprising contacting said population with a pesticidally-effective amount of the polypeptide of claim 1.

8. A method for killing a lepidopteran, coleopteran, nematode, or dipteran pest, comprising contacting said pest with, or feeding to said pest, a pesticidally-effective amount of the polypeptide of claim 1.

9. A method for producing a polypeptide with pesticidal activity, comprising culturing a host cell comprising a nucleic acid molecule encoding the polypeptide of claim 1 under conditions in which the nucleic acid molecule encoding the polypeptide is expressed.

* * * * *